(12) United States Patent
Cook et al.

(10) Patent No.: US 12,721,933 B2
(45) Date of Patent: Sep. 1, 2026

(54) METHODS OF MAKING AN INTERVENTIONAL MEDICAL DEVICE USEFUL IN PERFORMING TREATMENT UNDER MAGNETIC RESONANCE IMAGING

(71) Applicant: Cook Medical Technologies LLC, Bloomington, IN (US)

(72) Inventors: Carl A. Cook, Bloomington, IN (US); Sean D. Chambers, Bloomington, IN (US); Gary L. Neff, Bloomington, IN (US); Ram H. Paul, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 17/573,073

(22) Filed: Jan. 11, 2022

(65) Prior Publication Data

US 2022/0218881 A1 Jul. 14, 2022

Related U.S. Application Data

(60) Provisional application No. 63/135,918, filed on Jan. 11, 2021.

(51) Int. Cl.
*A61L 31/14* (2006.01)
*A61B 90/00* (2016.01)
(Continued)

(52) U.S. Cl.
CPC .............. *A61L 31/14* (2013.01); *A61B 90/00* (2016.02); *A61L 31/022* (2013.01); *B21B 3/00* (2013.01);
(Continued)

(58) Field of Classification Search
CPC ............................................ A61B 2017/00526
See application file for complete search history.

(56) References Cited

U.S. PATENT DOCUMENTS 4,471,204 A 9/1984 Takafuji
4,781,186 A 11/1988 Simpson
(Continued)

FOREIGN PATENT DOCUMENTS

AU 2002334881 4/2003
AU 2002358281 A1 7/2003
(Continued)

OTHER PUBLICATIONS

The extended European search report, Application No. 22150984.7, dated Dec. 5, 2022.
(Continued)

*Primary Examiner* — Sarang Afzali
(74) *Attorney, Agent, or Firm* — MacMillan, Sobanski & Todd, LLC

(57) ABSTRACT

Example interventional medical devices useful in performing treatment under magnetic resonance imaging and related methods are described. A method of making a medical device useful in procedures performed under magnetic resonance imaging includes selecting a first material, selecting a second material that is different from the first material, incorporating the second material into a portion of the first material, and forming the first and second materials into a desired structure to form the interventional medical device. The second material can be melted and disposed in a void formed in the first material, and work hardened to increase magnetic susceptibility.

23 Claims, 8 Drawing Sheets

(51) Int. Cl.
*A61L 31/02* (2006.01)
*B21B 3/00* (2006.01)
*B23P 15/00* (2006.01)
*C22F 1/10* (2006.01)
*A61B 17/00* (2006.01)

(52) U.S. Cl.
CPC ................ *B23P 15/00* (2013.01); *C22F 1/10* (2013.01); *A61B 2017/00526* (2013.01); *A61B 2090/374* (2016.02); *A61B 2090/3954* (2016.02)

(56) References Cited

U.S. PATENT DOCUMENTS 4,862,891 A 9/1989 Smith
5,053,004 A 10/1991 Markel
5,169,396 A 12/1992 Dowlatshahi et al.
5,228,441 A 7/1993 Lundquist
5,284,128 A 2/1994 Hart
5,291,890 A 3/1994 Cline et al.
5,315,996 A 5/1994 Lundquist
5,322,064 A 6/1994 Lundquist
5,322,505 A 6/1994 Krause
5,329,923 A 7/1994 Lundquist
5,346,473 A 9/1994 Bowman
5,362,478 A 11/1994 Desai et al.
5,380,304 A 1/1995 Parker
5,425,723 A 6/1995 Wang
5,454,787 A 10/1995 Lundquist
5,460,187 A 10/1995 Daigle
5,477,856 A 12/1995 Lundquist
5,507,766 A 4/1996 Kugo
5,573,520 A 11/1996 Schwartz
5,578,009 A 11/1996 Kraus et al.
5,605,543 A 2/1997 Swanson
5,685,868 A 11/1997 Lundquist
5,690,120 A 11/1997 Jacobsen et al.
5,728,079 A 3/1998 Weber
5,730,732 A 3/1998 Sardelis
5,741,429 A 4/1998 Donadio, III
5,755,714 A 5/1998 Murphy-Chutorian
5,792,055 A 8/1998 McKinnon
5,810,807 A 9/1998 Ganz et al.
5,813,996 A 9/1998 St. Germain et al.
5,833,632 A 11/1998 Jacobsen et al.
5,833,692 A 11/1998 Cesarini
5,853,375 A 12/1998 Orr
5,897,533 A 4/1999 Glickman
5,897,536 A 4/1999 Nap et al.
5,908,410 A 6/1999 Weber et al.
5,916,162 A 6/1999 Snelten et al.
5,922,003 A 7/1999 Anctil
5,951,494 A 9/1999 Wang et al.
6,017,319 A 1/2000 Jacobsen et al.
6,019,737 A 2/2000 Murata
6,059,769 A 5/2000 Lunn
6,093,185 A 7/2000 Ellis et al.
6,102,890 A 8/2000 Stivland
6,146,373 A 11/2000 Cragg
6,228,073 B1 5/2001 Noone
6,246,896 B1 6/2001 Dumoulin et al.
6,246,914 B1 6/2001 de la Rama
6,267,781 B1 7/2001 Tu
6,273,404 B1 8/2001 Holman
6,286,555 B1 9/2001 Pauker
6,350,253 B1 2/2002 Deniega
6,375,059 B2 4/2002 Ohnishi
6,394,976 B1 5/2002 Winston et al.
6,428,489 B1 8/2002 Jacobsen
6,430,429 B1 8/2002 Van Vaals
6,451,026 B1 9/2002 Biagtan et al.
6,458,088 B1 10/2002 Hurtak et al.
6,464,645 B1 10/2002 Park et al.
6,574,497 B1 6/2003 Pacetti
6,611,720 B2 8/2003 Hata
6,612,998 B2 9/2003 Gosiengfiao et al.
6,613,002 B1 9/2003 Clark et al.
6,623,491 B2 9/2003 Thompson
6,626,849 B2 9/2003 Huitema et al.
6,652,508 B2 11/2003 Griffin
6,675,033 B1 1/2004 Lardo et al.
6,687,533 B1 2/2004 Hirano et al.
6,695,781 B2 2/2004 Rabiner et al.
6,714,809 B2 3/2004 Lee et al.
6,749,560 B1 6/2004 Konstorum
6,772,000 B2 8/2004 Talpade
D496,728 S 9/2004 Holsinger
6,799,067 B2 9/2004 Pacetti et al.
6,845,259 B2 1/2005 Pacetti et al.
6,860,898 B2 3/2005 Stack
6,911,016 B2 6/2005 Balzum et al.
6,918,882 B2 7/2005 Skujins et al.
6,975,896 B2 12/2005 Ehnholm et al.
7,001,369 B2 2/2006 Griffin
7,074,197 B2 7/2006 Reynolds et al.
7,160,296 B2 1/2007 Pearson et al.
7,169,118 B2 1/2007 Reynolds et al.
7,182,735 B2 2/2007 Shireman et al.
7,278,973 B2 10/2007 Iwami et al.
7,347,829 B2 3/2008 Mark
7,507,211 B2 3/2009 Pacetti et al.
7,540,845 B2 6/2009 Parins
7,553,287 B2 6/2009 Reynolds et al.
7,596,402 B2 9/2009 Duerk et al.
7,618,379 B2 11/2009 Reynolds et al.
7,641,621 B2 1/2010 Crank
7,651,578 B2 1/2010 Sharrow et al.
7,708,751 B2 5/2010 Hughes et al.
7,747,314 B2 6/2010 Parins et al.
7,749,264 B2 7/2010 Gregorich
7,758,520 B2 7/2010 Griffin et al.
7,761,138 B2 7/2010 Wang et al.
7,778,682 B2 8/2010 Kumar et al.
7,785,273 B2 8/2010 Eskuri
7,789,906 B2 9/2010 Blank
7,792,568 B2 9/2010 Zhong et al.
7,833,175 B2 11/2010 Parins
7,841,994 B2 11/2010 Skujins et al.
7,848,788 B2 12/2010 Tulley
7,875,025 B2 1/2011 Cockburn et al.
7,914,467 B2 3/2011 Layman
7,918,819 B2 4/2011 Karmarkar
7,943,161 B2 5/2011 Carlgren et al.
7,989,042 B2 8/2011 Obara
7,993,286 B2 8/2011 Reynolds et al.
8,002,715 B2 8/2011 Shireman
8,007,434 B2 8/2011 Olson
8,021,311 B2 9/2011 Munoz et al.
8,048,004 B2 11/2011 Davis
8,048,030 B2 * 11/2011 McGuckin, Jr. ... A61B 17/3468 604/164.01
8,049,137 B2 11/2011 Holman
8,067,073 B2 11/2011 Zhong et al.
8,070,693 B2 12/2011 Ayala et al.
8,082,021 B2 12/2011 Hyde et al.
8,092,444 B2 1/2012 Lentz
8,105,246 B2 1/2012 Voeller
8,137,292 B2 3/2012 Skujins et al.
8,137,293 B2 3/2012 Zhou et al.
8,142,431 B2 3/2012 Ducharme
8,163,326 B2 4/2012 Zhong et al.
8,167,815 B2 5/2012 Parihar
8,167,821 B2 5/2012 Sharrow
8,182,444 B2 5/2012 Uber, III et al.
8,182,465 B2 5/2012 Griffin
8,211,116 B2 7/2012 Dostman, Jr. et al.
8,211,143 B2 * 7/2012 Stefanchik ......... A61B 17/0482 606/223
8,214,015 B2 7/2012 Macaulay et al.
8,257,279 B2 9/2012 Davis
8,257,358 B2 9/2012 Haddock et al.
8,262,563 B2 9/2012 Bakos
D669,577 S 10/2012 Holsinger
8,292,827 B2 10/2012 Musbach

(56) References Cited

U.S. PATENT DOCUMENTS 8,292,828 B2 10/2012 Uihlein
8,337,492 B2 12/2012 Kunis et al.
8,376,961 B2 2/2013 Layman et al.
8,396,532 B2 3/2013 Jenkins et al.
8,409,114 B2 4/2013 Parins
8,414,506 B2 4/2013 Reynolds et al.
8,419,658 B2 4/2013 Eskuri
8,478,381 B2 7/2013 Kocaturk
8,485,992 B2 7/2013 Griffin et al.
8,521,257 B2 8/2013 Whitcomb et al.
8,523,786 B2 9/2013 Von Weymarn-Scharli
8,526,691 B2 9/2013 Strehl
8,529,872 B2 9/2013 Frank et al.
8,535,243 B2 9/2013 Shireman
8,535,310 B2 9/2013 Hardin, Jr. et al.
8,540,648 B2 9/2013 Uihlein
8,551,020 B2 10/2013 Chen et al.
8,551,021 B2 10/2013 Voeller et al.
8,556,914 B2 10/2013 Vrba
8,620,406 B2 12/2013 Smith et al.
8,636,716 B2 1/2014 Griffin
8,684,953 B2 4/2014 Cabiri
8,728,010 B2 5/2014 Hirshman
8,728,116 B1 5/2014 Janardhan
8,740,957 B2 6/2014 Masotti
8,795,202 B2 8/2014 Northorp et al.
8,795,254 B2 8/2014 Layman et al.
8,846,006 B2 9/2014 Frank et al.
8,880,149 B2 11/2014 Barbot
8,932,270 B2 1/2015 Therese
9,038,639 B2 5/2015 Pfeffer et al.
9,072,874 B2 7/2015 Northrop et al.
9,138,561 B2 9/2015 Stenzel et al.
9,192,743 B2 11/2015 Stenzel et al.
9,227,037 B2 1/2016 Northrop
9,326,757 B2 5/2016 Ravikumar et al.
9,346,093 B2 5/2016 Cacace
9,375,195 B2 6/2016 Kamen
9,383,421 B2 7/2016 Vij
9,656,004 B2 5/2017 Duering et al.
9,669,240 B2 6/2017 Kohler et al.
9,687,681 B2 6/2017 Kohler et al.
9,775,523 B2 10/2017 Gregorich
9,861,450 B2 * 1/2018 Bolan .................... A61B 90/39
10,010,723 B2 7/2018 Koehler
10,028,666 B2 7/2018 Gregorich
10,035,002 B2 7/2018 Weiss
10,065,023 B2 9/2018 Sela
10,172,537 B2 1/2019 Pfeffer
10,201,333 B2 2/2019 Nock et al.
10,555,753 B2 2/2020 Krieger et al.
10,555,756 B2 2/2020 Krieger et al.
10,583,269 B2 3/2020 Burkholz et al.
10,695,540 B2 6/2020 Kocaturk
10,814,044 B2 10/2020 Duering
10,835,710 B2 11/2020 Lederman
10,953,195 B2 3/2021 Jalgaonkar et al.
10,976,388 B2 4/2021 Yang
11,034,580 B2 6/2021 Ostrovska
11,052,242 B1 7/2021 Gore
11,062,473 B2 7/2021 Fine
11,071,869 B2 7/2021 Leigh
11,090,033 B2 8/2021 Rebellino
11,090,130 B2 8/2021 Nemanic
11,097,017 B2 8/2021 Preihs
11,105,873 B2 8/2021 Poole
11,116,405 B2 9/2021 Partanen
11,142,826 B2 10/2021 Han
11,202,888 B2 12/2021 Paul, Jr.
11,219,761 B2 1/2022 Verzal
11,226,383 B2 1/2022 Sengupta
11,234,654 B2 2/2022 Han
11,241,296 B2 * 2/2022 Bolan ................ A61K 49/0447
11,260,222 B2 3/2022 Olsen
11,266,326 B2 3/2022 Dyer
11,298,567 B2 4/2022 Vahala
11,304,683 B2 4/2022 Mitra
11,318,280 B2 5/2022 Weiss
11,737,851 B2 8/2023 Paul
2002/0055449 A1 5/2002 Porta et al.
2002/0058868 A1 5/2002 Hoshino et al.
2002/0107446 A1 8/2002 Rabiner et al.
2002/0151787 A1 10/2002 Bjornerud et al.
2003/0055332 A1 3/2003 Daum et al.
2003/0055449 A1 3/2003 Lee et al.
2003/0060731 A1 3/2003 Fleischhacker
2003/0060842 A1 3/2003 Chin et al.
2003/0069520 A1 4/2003 Skujins et al.
2003/0069521 A1 4/2003 Reynolds et al.
2003/0100828 A1 5/2003 Engelhard et al.
2003/0100829 A1 * 5/2003 Zhong ..................... A61L 29/18
600/424
2003/0120148 A1 6/2003 Pacetti
2003/0135114 A1 7/2003 Pacetti et al.
2003/0167052 A1 9/2003 Lee
2003/0187461 A1 10/2003 Chin
2003/0208142 A1 11/2003 Boudewijn et al.
2004/0082946 A1 4/2004 Stewart et al.
2004/0082948 A1 4/2004 Stewart
2004/0097880 A1 5/2004 Schur
2004/0143180 A1 7/2004 Zhong et al.
2004/0167428 A1 8/2004 Quick et al.
2004/0167437 A1 8/2004 Sharrow et al.
2004/0167438 A1 8/2004 Sharrow
2004/0167439 A1 8/2004 Sharrow
2004/0167442 A1 8/2004 Shireman et al.
2004/0186377 A1 9/2004 Zhong et al.
2004/0193140 A1 9/2004 Griffin
2004/0199240 A1 10/2004 Dorn
2004/0200881 A1 10/2004 Gandy
2004/0254445 A1 12/2004 Bittner
2004/0254450 A1 12/2004 Griffin et al.
2005/0021002 A1 1/2005 Deckman
2005/0054952 A1 3/2005 Eskuri et al.
2005/0065437 A1 3/2005 Weber et al.
2005/0070793 A1 3/2005 Pacetti et al.
2005/0096665 A1 5/2005 Reynolds et al.
2005/0119615 A1 6/2005 Noriega et al.
2005/0125053 A1 6/2005 Yachia
2005/0143650 A1 * 6/2005 Winkel .................. A61B 90/39
600/423
2005/0148865 A1 7/2005 Weber
2005/0149009 A1 7/2005 Wakikaido et al.
2005/0165301 A1 7/2005 Smith et al.
2005/0215874 A1 9/2005 Wang
2005/0240165 A1 10/2005 Miki
2005/0277829 A1 12/2005 Tsonton
2005/0283215 A1 12/2005 Desinger et al.
2006/0004346 A1 1/2006 Begg
2006/0073101 A1 4/2006 Oldfield et al.
2006/0100687 A1 5/2006 Fahey
2006/0122537 A1 6/2006 Reynolds et al.
2006/0200048 A1 9/2006 Furst
2006/0253178 A1 11/2006 Masotti
2007/0016131 A1 1/2007 Munger et al.
2007/0026555 A1 2/2007 Lee
2007/0043333 A1 2/2007 Kampa et al.
2007/0060878 A1 3/2007 Bonnette et al.
2007/0083132 A1 4/2007 Sharrow
2007/0112331 A1 5/2007 Weber et al.
2007/0135734 A1 6/2007 Reyonlds et al.
2007/0149037 A1 6/2007 Souba et al.
2007/0162108 A1 7/2007 Carlson et al.
2007/0208405 A1 9/2007 Goodin
2007/0244414 A1 10/2007 Reynolds et al.
2007/0265551 A1 11/2007 Pfister
2007/0280850 A1 12/2007 Carlson
2008/0004689 A1 1/2008 Jahnke
2008/0021313 A1 1/2008 Eidenschink et al.
2008/0021347 A1 1/2008 Jacobsen
2008/0021400 A1 1/2008 Jacobsen
2008/0021401 A1 1/2008 Jacobsen
2008/0021402 A1 1/2008 Jacobsen
2008/0021403 A1 1/2008 Jacobsen

(56) References Cited

U.S. PATENT DOCUMENTS

2008/0021405 A1 1/2008 Jacobsen
2008/0021406 A1 1/2008 Jacobsen
2008/0021407 A1 1/2008 Jacobsen
2008/0021408 A1 1/2008 Jacobsen
2008/0045908 A1 2/2008 Gould et al.
2008/0077085 A1 3/2008 Eidenschink et al.
2008/0086047 A1 4/2008 McDaniel
2008/0097294 A1 4/2008 Prather et al.
2008/0097395 A1 4/2008 Adams
2008/0097398 A1 4/2008 Mitelberg et al.
2008/0097404 A1 4/2008 Yribarren
2008/0125674 A1 5/2008 Bilecen et al.
2008/0125766 A1 5/2008 Lubock
2008/0139925 A1 6/2008 Lubock
2008/0147001 A1 6/2008 Al-Marashi
2008/0194994 A1 8/2008 Bown
2008/0195194 A1 8/2008 Pacetti
2008/0262474 A1 10/2008 Northrop
2008/0269641 A1 10/2008 O'Shaughnessy et al.
2008/0272774 A1 11/2008 Bieri
2008/0294231 A1 11/2008 Aguilar
2008/0312597 A1 12/2008 Uihlein
2009/0036832 A1 2/2009 Skujins et al.
2009/0043228 A1 2/2009 Northrop
2009/0043283 A1 2/2009 Turnlund
2009/0043372 A1 2/2009 Northrop
2009/0117711 A1 5/2009 Harle
2009/0118675 A1 5/2009 Czyscon et al.
2009/0118704 A1 5/2009 Sharrow et al.
2009/0156961 A1 6/2009 Tsonton
2009/0177040 A1 7/2009 Lyons
2009/0177119 A1 7/2009 Heidner et al.
2009/0192584 A1 7/2009 Gerdts
2009/0227901 A1 9/2009 Hofmann
2009/0264731 A1 10/2009 Nour et al.
2009/0292225 A1 11/2009 Chen et al.
2010/0004562 A1 1/2010 Jalisi
2010/0030072 A1 2/2010 Casanova et al.
2010/0036364 A1 2/2010 Wuebbeling
2010/0063383 A1 3/2010 Anderson et al.
2010/0063479 A1 3/2010 Merdan et al.
2010/0069882 A1 3/2010 Jennings
2010/0087849 A1 4/2010 Griffin
2010/0145308 A1 6/2010 Layman
2010/0152612 A1 6/2010 Headley, Jr.
2010/0185080 A1 7/2010 Myhr
2010/0201361 A1 8/2010 Edelman
2010/0207291 A1 8/2010 Eidenschink
2010/0254897 A1 10/2010 Frank et al.
2010/0268325 A1 10/2010 Gregorich
2011/0022069 A1 1/2011 Mitusina
2011/0098554 A1 4/2011 Mardor et al.
2011/0160834 A1 6/2011 Aggerholm
2011/0166439 A1 7/2011 Pfeffer et al.
2011/0251519 A1 10/2011 Romoscanu
2011/0270169 A1 11/2011 Gardeski et al.
2011/0276034 A1 11/2011 Tomarelli
2011/0295217 A1 12/2011 Tanaka et al.
2012/0035434 A1 2/2012 Ferren et al.
2012/0053419 A1 3/2012 Bloom
2012/0053572 A1 3/2012 Rusu et al.
2012/0078087 A1 3/2012 Curry
2012/0083877 A1 4/2012 Nguyen et al.
2012/0108881 A1 5/2012 Chi Sing
2012/0133363 A1 5/2012 Mareci et al.
2012/0157935 A1 6/2012 Martin
2012/0172841 A1 7/2012 Kubo et al.
2012/0232658 A1 9/2012 Morgenstern et al.
2012/0265229 A1 10/2012 Rottenberg
2012/0268127 A1 10/2012 Cunningham et al.
2012/0289776 A1 11/2012 Keast
2012/0310080 A1 12/2012 Cunningham et al.
2013/0030362 A1 1/2013 Wright et al.
2013/0046285 A1 2/2013 Griffin
2013/0072904 A1 3/2013 Musbach
2013/0085444 A1 4/2013 Heinrich
2013/0123692 A1 5/2013 Zhang et al.
2013/0123768 A1 5/2013 Harlan
2013/0131496 A1 5/2013 Jenkins et al.
2013/0158478 A1 6/2013 Kaufmann et al.
2013/0165942 A1 6/2013 Tan-Malecki
2013/0231586 A1 9/2013 Tsonton
2013/0274591 A1 10/2013 Sonmez et al.
2013/0274618 A1 10/2013 Hou et al.
2013/0274711 A1 10/2013 O'Day
2013/0296718 A1 11/2013 Ranganathan
2013/0296903 A1 11/2013 Nita
2013/0304035 A1 11/2013 Cabiri
2013/0324837 A1 12/2013 Meyer et al.
2014/0005558 A1 1/2014 Gregorich
2014/0005647 A1 1/2014 Shuffler
2014/0031843 A1 1/2014 Rottenberg
2014/0039298 A1 2/2014 Whitcomb
2014/0053940 A1 2/2014 Konstorum
2014/0058275 A1 2/2014 Gregorich et al.
2014/0081134 A1 3/2014 Fortson
2014/0081244 A1 3/2014 Voeller et al.
2014/0121590 A1 5/2014 Degen
2014/0121642 A1 5/2014 Jordan et al.
2014/0180302 A1 6/2014 Vetter et al.
2014/0243615 A1 8/2014 Schaeffer et al.
2014/0243742 A1 8/2014 Pacheco et al.
2014/0350414 A1 11/2014 McGowan et al.
2014/0378916 A1 12/2014 Simpson
2015/0011834 A1 1/2015 Ayala
2015/0051583 A1 2/2015 Horvath
2015/0051696 A1 2/2015 Hou et al.
2015/0073391 A1 3/2015 Hutchins et al.
2015/0083284 A1 3/2015 Rawson
2015/0105796 A1 4/2015 Grace
2015/0148706 A1 5/2015 Abner
2015/0151081 A1 6/2015 Keith et al.
2015/0182671 A1 7/2015 Duering
2015/0190614 A1 7/2015 Uihlein
2015/0209551 A1 7/2015 Burdette
2015/0265167 A1 9/2015 McGowan et al.
2015/0335391 A1 11/2015 Linderman
2015/0338477 A1 11/2015 Schmidt et al.
2015/0342580 A1 12/2015 Clancy
2015/0351644 A1 12/2015 Lee et al.
2015/0374929 A1 12/2015 Hyde
2016/0008584 A1 1/2016 Root et al.
2016/0033059 A1 2/2016 Fonte
2016/0045190 A1 2/2016 Elfman
2016/0051384 A1 2/2016 Patel
2016/0051798 A1 2/2016 Weber et al.
2016/0082228 A1 3/2016 Sela
2016/0089515 A1 3/2016 Hansen et al.
2016/0158509 A1 6/2016 Wedan et al.
2016/0317212 A1 11/2016 Ge et al.
2017/0055908 A1 3/2017 Radman et al.
2017/0106171 A1 4/2017 Flores et al.
2017/0143317 A1 5/2017 Hoffman
2017/0165456 A1 6/2017 Tutungi
2017/0202480 A1 7/2017 Kim et al.
2017/0232158 A1 8/2017 Duering et al.
2017/0239450 A1 8/2017 Kocaturk et al.
2017/0291013 A1 10/2017 Pereira et al.
2017/0347913 A1 12/2017 Isaacson et al.
2017/0348509 A1 12/2017 Burkholz et al.
2018/0078742 A1 3/2018 Butler et al.
2018/0078743 A1 3/2018 Kubo
2018/0085027 A1 3/2018 Kimmel et al.
2018/0085184 A1 3/2018 Bolan
2018/0140801 A1 5/2018 Voss
2018/0161121 A1 6/2018 Butler et al.
2018/0185618 A1 7/2018 Sweeney
2018/0193606 A1 7/2018 Patel et al.
2018/0193608 A1 7/2018 Bodewadt et al.
2018/0243530 A1 8/2018 Lederman et al.
2018/0289388 A1 10/2018 Lenker
2018/0303603 A1 10/2018 Melsheimer et al.
2019/0046684 A1 2/2019 Roth
2019/0083071 A1 3/2019 Rebellino et al.

(56) References Cited

U.S. PATENT DOCUMENTS

| | | | | |
|---|---|---|---|---|
| 2019/0167952 | A1 | 6/2019 | Paul, Jr. | |
| 2019/0192124 | A1 | 6/2019 | Park | |
| 2019/0223975 | A1 | 7/2019 | Agostinelli et al. | |
| 2019/0351182 | A1 | 11/2019 | Chou | |
| 2019/0366036 | A1 | 12/2019 | Jalgaonkar et al. | |
| 2019/0374279 | A1 | 12/2019 | Weitzner et al. | |
| 2020/0000545 | A1* | 1/2020 | Paul | C21D 7/02 |
| 2020/0008678 | A1 | 1/2020 | Barbagli et al. | |
| 2020/0069927 | A1 | 3/2020 | Malek | |
| 2020/0121415 | A1 | 4/2020 | Mayes et al. | |
| 2021/0077077 | A1 | 3/2021 | Mitra et al. | |
| 2021/0106791 | A1 | 4/2021 | Uihlein | |
| 2021/0177510 | A1 | 6/2021 | Papaioannou | |
| 2021/0178121 | A1 | 6/2021 | Burdette | |
| 2021/0187253 | A1 | 6/2021 | Borm | |
| 2021/0208225 | A1 | 7/2021 | Gilbo | |
| 2021/0220624 | A1 | 7/2021 | Blacker | |
| 2021/0228841 | A1 | 7/2021 | Falb | |
| 2021/0236017 | A1 | 8/2021 | Pfeffer | |
| 2021/0247472 | A1 | 8/2021 | Kocaturk et al. | |
| 2021/0251696 | A1 | 8/2021 | Krueckers | |
| 2021/0255261 | A1 | 8/2021 | Li et al. | |
| 2021/0267696 | A1 | 9/2021 | Degertekin | |
| 2021/0275155 | A1 | 9/2021 | Hautvast | |
| 2021/0282866 | A1 | 9/2021 | Kamal | |
| 2021/0295985 | A1 | 9/2021 | Prokle | |
| 2022/0015636 | A1 | 1/2022 | Mak | |
| 2022/0050154 | A1 | 2/2022 | Schneider | |
| 2022/0088353 | A1 | 3/2022 | Paul, Jr. | |
| 2022/0096116 | A1 | 3/2022 | McFarland et al. | |
| 2022/0101576 | A1 | 3/2022 | Kaushik | |
| 2022/0104913 | A1 | 4/2022 | Blair | |
| 2022/0218881 | A1 | 7/2022 | Cook | |
| 2023/0248241 | A1 | 8/2023 | Anttila et al. | |
| 2023/0414967 | A1 | 12/2023 | Popowski | |
| 2024/0310462 | A1 | 9/2024 | Udale et al. | |
| 2025/0025260 | A1 | 1/2025 | Udale et al. | |
| 2025/0255693 | A1 | 8/2025 | Udale et al. | |

FOREIGN PATENT DOCUMENTS

| | | | |
|---|---|---|---|
| CA | 2094250 | | 6/1992 |
| CA | 2462335 | | 4/2003 |
| CN | 2930741 | | 8/2007 |
| CN | 106943218 | | 7/2017 |
| CN | 112426611 | A | 3/2021 |
| DE | 19843427 | | 3/2000 |
| DE | 20019484 | | 5/2001 |
| DE | 10029738 | | 1/2002 |
| DE | 20017836 | | 2/2002 |
| DE | 10243261 | A1 | 3/2004 |
| DE | 60208057 | T2 | 6/2006 |
| DE | 102005022688 | A1 | 11/2006 |
| DE | 102005030472 | | 1/2007 |
| DE | 202010004107 | U1 | 7/2010 |
| DE | 202010016473 | U1 | 2/2012 |
| DE | 102011101680 | A1 | 9/2012 |
| DE | 102011081445 | | 2/2013 |
| EP | 0315290 | | 5/1989 |
| EP | 0561903 | B1 | 7/1995 |
| EP | 0744186 | | 11/1996 |
| EP | 0775500 | | 5/1997 |
| EP | 0937481 | | 8/1999 |
| EP | 0628288 | B1 | 4/2000 |
| EP | 1116476 | A2 | 7/2001 |
| EP | 1551490 | A1 | 7/2005 |
| EP | 1432467 | | 12/2005 |
| EP | 1656963 | A1 | 5/2006 |
| EP | 1596894 | | 6/2006 |
| EP | 1011491 | | 1/2007 |
| EP | 1242138 | | 5/2007 |
| EP | 2228094 | A1 | 9/2010 |
| EP | 2364746 | | 9/2011 |
| EP | 2478927 | | 7/2012 |
| EP | 1819374 | | 8/2012 |
| EP | 2675353 | | 12/2013 |
| EP | 2762189 | A1 | 8/2014 |
| EP | 3093037 | | 11/2016 |
| EP | 2508213 | | 3/2018 |
| EP | 2508213 | B1 | 3/2018 |
| EP | 3288629 | | 3/2018 |
| EP | 3349650 | | 7/2018 |
| EP | 3586763 | A2 | 1/2020 |
| EP | 3610913 | | 2/2020 |
| EP | 3586763 | A3 | 3/2020 |
| EP | 4008388 | | 6/2022 |
| JP | 6032553 | | 7/1985 |
| JP | H10248853 | | 9/1998 |
| JP | 1998290839 | | 11/1998 |
| JP | H10314137 | | 12/1998 |
| JP | H11285533 | | 10/1999 |
| JP | 2005528126 | | 9/2005 |
| JP | 2005334645 | | 12/2005 |
| JP | 2006501974 | | 1/2006 |
| JP | 2006520645 | | 9/2006 |
| JP | 3962724 | | 8/2007 |
| JP | 2008515563 | | 5/2008 |
| JP | 2008272464 | | 11/2008 |
| JP | 2009512475 | | 3/2009 |
| JP | 2009183765 | A | 8/2009 |
| JP | 2010517722 | | 5/2010 |
| JP | 4494782 | B2 | 6/2010 |
| JP | 2019521743 | | 8/2019 |
| JP | 2020022737 | | 2/2020 |
| JP | 20200022737 | | 2/2020 |
| NL | 1006612 | | 1/1999 |
| WO | 9011313 | | 10/1990 |
| WO | 9601664 | | 1/1996 |
| WO | WO199842268 | | 10/1998 |
| WO | WO9855016 | | 12/1998 |
| WO | 0007652 | | 2/2000 |
| WO | WO20000064003 | | 1/2001 |
| WO | 01045786 | | 6/2001 |
| WO | WO0195794 | | 12/2001 |
| WO | 2002055146 | | 7/2002 |
| WO | 03030982 | | 4/2003 |
| WO | 03057302 | A1 | 7/2003 |
| WO | WO200303982 | | 7/2003 |
| WO | WO2003057302 | | 7/2003 |
| WO | WO2003092791 | | 11/2003 |
| WO | 2004075941 | | 9/2004 |
| WO | 2005112778 | | 12/2005 |
| WO | 2006063106 | | 6/2006 |
| WO | WO2006036786 | | 6/2006 |
| WO | 2006116538 | A2 | 11/2006 |
| WO | WO2006119645 | | 11/2006 |
| WO | 2007045913 | | 4/2007 |
| WO | 2010103762 | | 9/2010 |
| WO | 2011008538 | | 1/2011 |
| WO | WO2012032881 | | 3/2012 |
| WO | 2012112829 | | 8/2012 |
| WO | WO2016064753 | | 4/2016 |
| WO | 2016175882 | | 11/2016 |
| WO | 2016176393 | | 11/2016 |
| WO | WO2017048759 | | 3/2017 |
| WO | 2018182701 | A1 | 10/2018 |
| WO | 2021081079 | | 4/2021 |

OTHER PUBLICATIONS

Partial European Search Report, Application No. 22150984.7, dated Aug. 26, 2022.

Carpenter Corporation. "Magnetic Properties of Stainless Steels," pp. 1-9. Retrieved from Internet May 3, 2018.

Basar et al. "Segmented nitinol guidewires with stiffness-matched connectors for cardiovascular magnetic resonance catheterization: preserved mechanical performance and freedom from heating," J. Cardiovascular Magnetic Resonance (2015) 17:105. Published Nov. 30, 2015.

European Patent Office. "Supplementary European Search Report" for EP application No. 01942159, completed Feb. 2, 2006.

(56) References Cited

OTHER PUBLICATIONS

International Searching Authority, International Search Report and Written Opinion for international application No. PCT/US2018/063562, mailed Sep. 26, 2019, pp. 1-10.
The Extended European Search Report, Application No. 19183472.0, dated Feb. 13, 2020.
The Partial European Search Report, Application No. 19183472.0, dated Nov. 6, 2019.
US Office Action (Notice of Allowance), U.S. Appl. No. 17/539,683, dated Mar. 31, 2023.
Weitschies et al., "Magnetic Markers as a Noninvasive Tool To Monitor Gastrointestinal Transit", IEEE, Transactions on Biomedical Engineering, (1994), vol. 41, No. 2, doi: 10.1109/10.284931, ISSN 0018-9294, pp. 192-195.
Yeung et al., "Minimizing RF heating of conducting wires in MRI", Magnetic Resonance in Medicine: An Official Journal of the International Society for Magnetic Resonance in Medicine,( 2007), vol. 58 No. 5, pp. 1028-1034.
Yeung et al., "RF safety of wires in interventional MRI: using a safety index", Magnetic Resonance in Medicine: An Official Journal of the International Society for Magnetic Resonance in Medicine, (2002), vol. 47, No. 1, pp. 187-193.
Campbell-Washburn et al., "Opportunities in interventional and diagnostic imaging by using high-performance low-field-strength MRI", Radiology, (2019), vol. 293, No. 2, pp. 384-393.
Dempsey et al., "Investigation of the factors responsible for burns during MRI", Journal of Magnetic Resonance imaging: An Official Journal of the International Society for Magnetic Resonance in Medicine, (2001), vol. 13, No. 4, pp. 627-631.
Dempsey et al., "MRI safety review", In Seminars in Ultrasound, CT and MRI, (2002), vol. 23, No. 5, pp. 392-401. Abstract Only.
Etezadi-Amoli et al., "Controlling radiofrequency-induced currents in guidewires using parallel transmit", Magnetic resonance in medicine, (2015), vol. 74, No. 6, pp. 1790-1802.
European Communication Examination Report, Application No. 17178169.3, dated Aug. 7, 2019.
European Communication pursuant to Article 94 (3) EPC, Application No. 18829568.7, dated Jan. 30, 2024.
European Communication pursuant to Article 94 (3) EPC, Application No. 18829568.7, dated Mar. 24, 2022.
European Communication pursuant to Article 94(3) EPC, Application No. 19183472.0, dated Nov. 11, 2021.
European Communication pursuant to Article 96(2) EPC, Applcation No. 01942159.3, dated Jun. 14, 2006.
European Communication pursuant to Rule 161(1) and 162 EPC, Application No. 23713226.1, dated Sep. 17, 2024.
European extended Search Report, Application No. 17178169, dated Nov. 13, 2017.
European extended Search Report, Application No. 19183472.0, dated Feb. 13, 2020.
European Partial Search Report, Application No. 19183472.0, mailed Nov. 6, 2019.
European Patent Office "Examination Report" for European application No. 17178169.3, dated Aug. 7, 2019.
European Patent Office. "Supplementary European Search Report" Application No. 01942159, completed Feb. 2, 2006.
European Supplementary Search Report, Application No. 01942159.3, completed Feb. 10, 2006.
Fichtinger et al., "Transrectal Prostate Biopsy Inside Closed MRI Scanner with Remote Actuation, under Real-Time Image Guidance", MICCAI, (2002), 5th International Conference, Tokyo, Japan, pp. 91-98.
Google Patents Translation of Chinese Application No. CN106943218A, retreived from the Internet, May 23, 2024.
HiWire, Nitinol Core Wire Guide: Data Sheet, "Gain ureteral access with control.", Cook (2013).
Japanese 1st Office Action, Application No. 2019-121677, dated Apr. 18, 2023.
Japanese Office Action, Application No. 2023139741, dated May 7, 2024.
Kivelitz et al., "A Vascular Stent as an Active Component for Locally Enhanced Magnetic Resonance Imaging: Initial in Vivo Imaging Results After Catheter-guided Placements in Rabbits", Investigative Radiology, (2003), vol. 38, No. 3, pp. 147-152.
Kivelitz et al., "The Active Magnetic Resonance Imaging Stent (AMRIS): Initial Experimental In Vivo Results with Locally Amplified MR Angiography and Flow Measurements", (2001), Investigative Radiology, vol. 36, No. 11, pp. 625-631.
Konings et al., "Heating around intravascular guidewires by resonating RF waves", Journal of Magnetic Resonance Imaging, (2000), vol. 12, pp. 79-85.
Kuehne Titus et al, "Pair of resonant fiducial markers for localization of endovascular catheters at all catheter orientations", Journal of Magnetic Resonance Imaging, Society for Magnetic Resonance Imaging, Oak Brook, IL, US, (2011), vol. 17, No. 5, doi:10.1002/JMRI.10307, ISSN 1053-1807, pp. 620-624.
Ladd et al., "Reduction of resonant RF heating in intravascular catheters using coaxial chokes", Magnetic Resonance in Medicine: An Official Journal of the International Society for Magnetic Resonance in Medicine, (2000), vol. 43, No. 4, pp. 615-619.
Martin et al., "MR imaging during endovascular procedures: an evaluation of the potential for catheter heating," Magnetic Resonance in Medicine: An Official Journal of the International Society for Magnetic Resonance in Medicine, (2009), vol. 61, No. 1, pp. 45-53.
Nano4Imaging, Your Health—Our Vision, MR wire guidewire: Technical Specification, retrieved from Internet on Sep. 6, 2023, URL: https://www.nano4imaging.com/#EmeryGlide.
Nitz et al., "On the heating of linear conductive structures as guide wires and catheters in interventional MRI", Journal of Magnetic Resonance Imaging, (2001), vol. 13, No. 1, pp. 105-114.
PCT International Search Report and Written Opinion, Application No. PCT/US2016/029661, dated Jul. 27, 2016.
PCT International Search Report and Written Opinion, Application No. PCT/US2018/063562, mailed Sep. 26, 2019.
PCT International Search Report and Written Opinion, Application No. PCT/US2023/030307, dated Dec. 18, 2023.
PCT International Search Report and Written Opinion, Application No. PCT/US2023/062094, dated May 9, 2023.
PCT International Search Report and Written Opinion, Application No. PCT/US2023/062097, dated Jul. 13, 2023.
PCT International Search Report and Written Opinion, Application No. PCT/US2023/062104, dated Jun. 14, 2023.
PCT International Search Report, Application No. PCT/US2016/029670, dated Jul. 15, 2016.
Pictet et al., "Radiofrequency heating effects around resonant lengths of wire in MRI", Physics in Medicine & Biology, (2002), vol. 47 No. 16, 2973-2985, Abstract Only.
Tong et al., "Practical aspects of MR imaging in the presence of conductive guide wires", Physics in Medicine & Biology, (2009), vol. 55 No. 1, Abstract Only.
US Office Action (Ex Parte Quayle) U.S. Appl. No. 16/454,905, dated Mar. 2, 2023.
US Office Action (Final Rejection) U.S. Appl. No. 17/573,073, dated Jul. 22, 2024.
US Office Action (Final), U.S. Appl. No. 17/573,104, dated May 30, 2024.
US Office Action (Final), U.S. Appl. No. 17/573,189, dated Dec. 19, 2024.
US Office Action (Non-Final Rejection) U.S. Appl. No. 17/573,073, dated Jan. 31, 2024.
US Office Action (Non-Final Rejection) U.S. Appl. No. 18/106,601, dated Nov. 18, 2024.
US Office Action (Non-Final) U.S. Appl. No. 16/454,905, dated Oct. 13, 2022.
US Office Action (Non-Final), U.S. Appl. No. 16/207,391, dated Feb. 19, 2021.
US Office Action (Non-Final), U.S. Appl. No. 17/539,683, dated Dec. 8, 2022.
US Office Action (Non-Final), U.S. Appl. No. 17/573,104, dated Dec. 22, 2023.
US Office Action (Non-Final), U.S. Appl. No. 17/573, 189, dated Jun. 24, 2024.

(56) References Cited

OTHER PUBLICATIONS

US Office Action (Non-Final), U.S. Appl. No. 18/233,519, dated Mar. 5, 2024.
Japanese Notification of Reason for Rejection, Application No. 2023-139741, mailed Jan. 8, 2025.
U.S. Office Action (Non-Final) U.S. Appl. No. 18/238,747, dated Mar. 14, 2025.
European Patent Office "Communication pursuant to Article 94(3)", App.ication No. 23 718 542.6, dated May 16, 2025.
Nour et al., "Magnetic Resonance Image-Guided Focal Prostate Ablation", (2016), Seminars In Interventional Radiology, vol. 33, No. 3, pp. 206-216.
Yun et al., "Breast Magnetic Resonance Imaging-Guided Biopsy", J Korean Soc Radiol. (2016), 74(6), pp. 351-360.
U.S. Office Action (Non-Final Rejection) for U.S. Appl. No. 17/573,087, dated Apr. 22, 2025.
U.S. Office Action (Non-Final Rejection) for U.S. Appl. No. 17/573,189, dated May 14, 2025.
U.S. Office Action (Final Rejection) for U.S. Appl. No. 18/106,601, dated Jun. 2, 2025.
U.S. Office Action (Non-Final Rejection) for U.S. Appl. No. 18/238,747, dated Jul. 1, 2025.
U.S. Office Action (Non-Final Rejection) for U.S. Appl. No. 18/234,440, dated Aug. 27, 2025.
Japanese Notification of Refusal, Application No. 2022002110, dated Oct. 8, 2025.
European extended search report, Application No. 251968681 dated Jan. 21, 2026.
U.S. Office Action (Notice of Allowance) for U.S. Appl. No. 18/234,440, dated Jan. 28, 2026.
Basar et al., "Susceptibility artifacts from metallic markers and cardiac catheterization devices on a high-performance 0.55 T MRI system", Magnetic Resonance Imaging, (2021), vol. 77, pp. 14-20.
U.S. Office Action (Non-Final Rejection) for U.S. Appl. No. 18/836,215, mailed Jul. 24, 2025.
U.S. Office Action (Non-Final Rejection) for U.S. Appl. No. 18/923,852, mailed Nov. 3, 2025.
U.S. Office Action (Final Rejection) for U.S. Appl. No. 18/836,215 dated Jan. 2, 2026.
U.S. Office Action (Non-Final Rejection) for U.S. Appl. No. 18/106,601, dated Jan. 9, 2026.
Cross et al., "Nitinol Characterization Study," Issued by Originator as Report No. GER-14188, (1969), NASA CR-1433, pp. 1-60.
European Communication pursuant to Article 94(3), Application No. 23718542.6, dated Dec. 9, 2025.
U.S. Office Action (Final Rejection) for U.S. Appl. No. 18/238,747, dated Dec. 16, 2025.
U.S. Office Action (Non-Final Rejection) for U.S. Appl. No. 19/027,914, dated Dec. 18, 2025.
U.S. Office Action (Final Rejection) for U.S. Appl. No. 19/027,914, dated May 29, 2026.
European Communication pursuant to Article 94(3), Application No. 23713226.1, dated May 29, 2026.
U.S. Office Action (Non-Final Rejection) for U.S. Appl. No. 18/836,258, dated Jun. 24, 2026.
U.S. Office Action (Non-Final Rejection) for U.S. Appl. No. 18/238,747, dated Jun. 29, 2026.
U.S. Office Action (Non-Final Rejection) for U.S. Appl. No. 18/836,215, dated Jul. 1, 2026.
Peeters et al., "Development and testing of passive tracking markers for different field strengths and tracking speeds," Physics in Medicine & Biology, (2006), vol. 51(6), pp. N127-N137.

* cited by examiner

METHODS OF MAKING AN INTERVENTIONAL MEDICAL DEVICE USEFUL IN PERFORMING TREATMENT UNDER MAGNETIC RESONANCE IMAGING

RELATED APPLICATIONS

This application claims priority to U.S. Provisional Application No. 63/135,918, filed Jan. 11, 2021. The entire contents of this related application are hereby incorporated by reference into this disclosure.

FIELD

The disclosure relates generally to the field of medical devices. More particularly, the disclosure relates to interventional medical devices useful in performing treatment under magnetic resonance imaging (MRI), imaging methods, methods of performing interventional medical treatment under MRI, and methods of making medical devices.

BACKGROUND

Interventional procedures conducted under MRI have several benefits over X-Ray-guided interventions. For example, the patient is not exposed to ionizing radiation. Also, MRI provides the ability to characterize tissue and fluid flow during an interventional procedure. For at least these reasons, the use of interventional MRI is gaining wider acceptance and the number of procedures that can be performed under MRI is generally increasing.

The art provides only a limited number of interventional medical devices suitable for use under MRI, however, which continues to limit growth of the use of interventional MRI procedures. As a result, patients have not yet benefitted fully from interventional MRI technologies and, indeed, are often still limited to less convenient, and potentially less effective, options for certain treatments.

For example, without interventional MRI, addressing some conditions requires the use of multiple imaging modalities over the clinical path from initial testing to treatment. On a practical level, this use of multiple imaging modalities can require multiple patient visits to a healthcare facility. A conventional approach to the treatment of prostate cancer is illustrative—visualization, biopsy, and treatment are performed over the course of three separate patient visits. At a first visit, a scan is completed using a magnetic resonance scanner to produce an image showing the prostate and any abnormalities. The patient then leaves the facility and awaits a review of the image. If abnormalities exist, a second patient visit will occur such that a biopsy sample of the abnormal tissue can be completed. Software is used to merge magnetic resonance images with the procedural ultrasound to provide guidance in conducting the biopsy. This fusion decreases the value of the diagnostic magnetic resonance image. The patient then leaves the facility again and awaits a review of the biopsy sample to determine whether further treatment is required (e.g., if the review results in a positive prostate cancer diagnosis). If further treatment is required, the patient must visit the facility a third time for delivery of the treatment. Completion of these three patient visits often extends over months, prevents the patient from receiving rapid treatment, and increases the overall costs associated with treatment, both to the patient and to the healthcare providers involved. Furthermore, the use of software to merge images from multiple imaging modalities, such as magnetic resonance images and ultrasound images, has drawbacks, such as image overlay or alignment issues and the potential for compression shifting of tissues. Ultimately, these drawbacks of current treatment approaches can limit the overall effectiveness of the treatment. Interventional MRI has the potential to overcome these drawbacks by enabling A need exists, therefore, for new and improved interventional medical devices useful in performing treatment under MRI, imaging methods, methods of performing interventional medical treatment under MRI, and methods of making medical devices.

BRIEF SUMMARY OF SELECTED EXAMPLES

Various example interventional medical devices useful in performing treatment under MRI, imaging methods, methods of performing interventional medical treatment under MRI, and methods of making medical devices are described herein.

An example interventional medical device useful in performing treatment under MRI includes a main body that has a central lengthwise axis, a proximal end, a distal end, and an axial length. The main body is formed of a first MRI compatible material. A marker is disposed along the entire axial length of the main body and parallel to the lengthwise axis. The marker is formed of a second MRI compatible material that is different than the first material.

Another example interventional medical device useful in performing treatment under MRI includes an elongate tubular member and a plurality of markers. The elongate tubular member has a main body that has a central lengthwise axis, a proximal end, a distal end, an axial length, and defines a proximal opening, a distal opening, and a lumen that extends from the proximal opening to the distal opening. The plurality of markers is disposed along a portion of the axial length of the main body and parallel to the lengthwise axis. Each marker of the plurality of markers is attached to the main body. The elongate tubular member is formed of a first material and each marker of the plurality of markers is formed of a second material that is different than the first material and incorporated into the first material.

Another example interventional medical device useful in performing treatment under MRI includes and elongate tubular member and a marker attached to the elongate tubular member. The elongate tubular member has a first main body and a second main body. The first main body has a central lengthwise axis, a proximal end, a distal end, and defines a proximal opening, a distal opening, and a lumen that extends from the proximal opening to the distal opening. The second main body has a central lengthwise axis, a proximal end, a distal end, and defines a proximal opening, a distal opening, and a lumen that extends from the proximal opening of the second main body to the distal opening of the second main body. The marker is disposed along a portion of the axial length of the first main body and parallel to the central lengthwise axis of the first main body. The marker is attached to an external surface of the first main body and is formed of Gadolinium. The second main body is bonded over the external surface of the first main body such that the marker is completely disposed between the first and second main bodies.

Another example interventional medical device useful in performing treatment under MRI includes and elongate tubular member and a marker attached to the elongate tubular member. The elongate tubular member has a main body that has a central lengthwise axis, a proximal end, a distal end, and defines a proximal opening, a distal opening, and a lumen that extends from the proximal opening to the distal opening. The main body is formed of 304 Stainless Steel. The marker is disposed along a portion of the axial length of the main body and parallel to the central lengthwise axis of the main body. The marker comprises a portion of the main body that includes dimpling or peening such that individual areas of the main body have been hardened.

An example imaging method comprises selecting an interventional medical device that has a main body that has proximal and distal ends and a marker attached to the main body; advancing the distal end of the interventional medical device to a first location within a bodily passage of a patient and until the marker is disposed at a second location within the bodily passage; scanning a portion of the bodily passage that includes the first and second locations within the bodily passage using a magnetic resonance scanner; obtaining a magnetic resonance image of the portion of the bodily passage such that the image includes an artifact indicative of the presence of the marker within the portion of the bodily passage; and withdrawing the interventional medical device from the bodily passage.

An example method of performing an interventional medical treatment comprises selecting an interventional medical device having a main body that has proximal and distal ends and a marker attached to the main body; advancing the distal end of the interventional medical device to a first location within a bodily passage of a patient and until the marker is disposed at a second location within the bodily passage; scanning a portion of the bodily passage that includes the second location within the bodily passage using a magnetic resonance scanner; obtaining a magnetic resonance image of the portion of the bodily passage such that the image includes an artifact indicative of the presence of the marker within the portion of the bodily passage; viewing an artifact in the image generated by the presence of the marker; manipulating the interventional medical device based on the location of the artifact relative to the bodily passage; and withdrawing the interventional medical device from the bodily passage.

An example method of making a medical device comprises selecting a first material to form an interventional medical device; selecting a second material to form a marker to be included in a portion of the interventional medical device; incorporating the second material into a portion of the first material; and forming the first and second materials into a desired structure to form the interventional medical device.

Another example method of making a medical device comprises selecting an interventional medical device precursor that has a main body that has proximal and distal ends; selecting a marker; and attaching the marker to the main body.

An example method of performing an interventional medical treatment comprises selecting an interventional medical device having a main body that has proximal and distal ends and a marker attached to the main body; advancing the distal end of the interventional medical device to a first location within a bodily passage of a patient and until the marker is disposed at a second location within the bodily passage; scanning a portion of the bodily passage that includes the second location within the bodily passage using a magnetic resonance scanner; obtaining a magnetic resonance image of the portion of the bodily passage such that the image includes an artifact indicative of the presence of the marker within the portion of the bodily passage; viewing an artifact in the image generated by the presence of the marker; manipulating the interventional medical device based on the location of the artifact relative to the bodily passage; and withdrawing the interventional medical device from the bodily passage.

Additional understanding of these example interventional medical devices, imaging methods, methods of performing interventional medical treatment under MRI, and methods of making medical devices can be obtained by review of the detailed description of selected examples, below, and the references drawings.

DETAILED DESCRIPTION OF SELECTED EXAMPLES

The following detailed description and the appended drawings describe and illustrate various example interventional medical devices, imaging methods, methods of performing interventional medical treatment under MRI, and methods of making medical devices. The description and illustration of these examples are provided to enable one skilled in the art to make and use an interventional medical device and to perform imaging methods, methods of performing interventional medical treatment under MRI, and methods of making interventional medical devices. They are not intended to limit the scope of the invention, or its protection, in any manner. The invention is capable of being practiced or carried out in various ways and the examples described and illustrated herein are not considered exhaustive.

As used herein, the term “attached” refers to one member being secured to another member such that the members do not completely separate from each other during use performed in accordance with the intended use of an item that includes the members in their attached form.

As used herein, the term “circumference” refers to an external enclosing boundary of a body, element, or feature and does not impart any structural configuration on the body, element, or feature.

As used herein, the term “marker” refers to a discrete deposit of a first material on a second material such that the first material is visible under MRI and is distinguishable from the second material under MRI, a portion of an interventional device in which a first material has been incorporated into a second material such that the combination of the first and second materials is visible under MRI and is distinguishable from the second material under MRI, and a portion of an interventional device in which a material that forms a portion of an interventional device has been manipulated such that the portion is visible under MRI and is distinguishable from the remainder of the interventional device under MRI.

As used herein, the term "passive," in relation to a marker, refers to a marker that is either unpowered or powered exclusively by the electromagnetic field of a magnetic resonance scanner.

As used herein, the term "treatment" refers to a medical procedure performed on or in a portion of a body of a patient. Examples of treatments include delivery of an agent to a site within a body vessel, modification of a local environment inside of a body vessel such as by heating or cooling, and removal of a tissue or portion of a tissue from a site within a body of a patient (i.e., biopsy).

Figure 1:
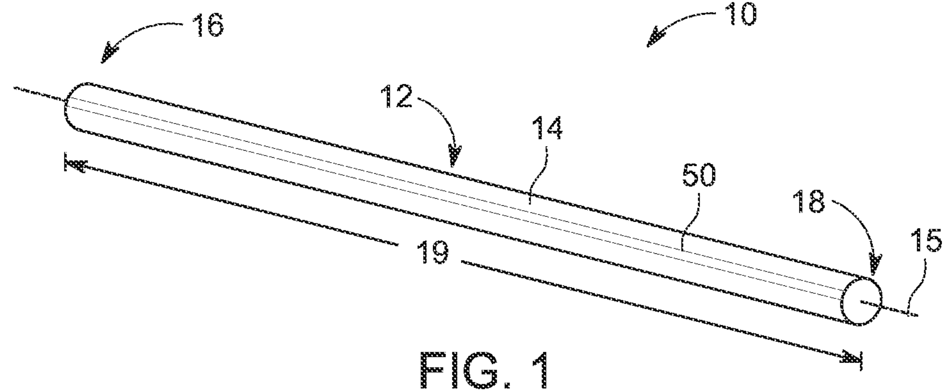
FIG. 1 is a perspective view of a first example interventional medical device.

FIG. 1 illustrates a first example interventional medical device 10. In this example, the interventional medical device 10 is a guidewire 12.

The guidewire 12 has a main body 14 that has a central lengthwise axis 15, a proximal end 16, a distal end 18, and an axial length 19. The axial length 19 extends from the proximal end 16 to the distal end 18. The guidewire 12 is a flexible member, can comprise any suitable structure, and can be formed of any suitable material. In the illustrated embodiment, the guidewire is an elongate tubular member formed of a polymer and defining an internal lumen. Additional components, such as coils and the like, can be included in the guidewire 12 in conventional manner.

In this example, a marker 50 is disposed along the entire axial length 19 of the main body 14 and parallel to the lengthwise axis 15. The marker 50 comprises a magnetically susceptible material and is disposed on and attached to an external surface of the main body 14. In some embodiments, the marker 50 is incorporated into the material forming the main body 14. For example, a ferromagnetic or paramagnetic compound can be incorporated into the material that forms the main body 14 during manufacture and at a desired location on the main body 14. Examples of materials considered suitable to incorporate into a material that forms a main body 14 include ferromagnetic and paramagnetic compounds, such as those in powder form, Tantalum powder, Barium Sulfate, Bismuth Oxychloride, Tungsten, Iron Oxide nanoparticles, functionalized magnetite, Gadolinium, Stainless Steel, Ferritic Stainless Steel, Ferritic Stainless Steel powders, 316 Stainless Steel, and any other material considered suitable for a particular embodiment. Alternative to incorporating a marker into the material that forms an interventional medical device, alternative embodiments can include a marker disposed on a surface of the main body, such as an internal or external surface. For example, a marker can be printed onto, adhered to, or electroplated onto a surface of a main body forming the interventional medical device, such as an internal or external surface. For example, in embodiments in which an interventional medical device is formed of a metal, an ink containing a magnetically susceptible material, such as an ink containing magnetic particles, an ink containing Iron Oxide nanoparticles, or an ink containing Iron Oxide nanoparticles bound to phospholipids, can be printed onto an external surface or an internal surface of a main body to form a marker. Also alternatively, a tape including a magnetically susceptible material, such as magnetic tape, can be adhered to an external surface or an internal surface of a main body of the interventional medical device. Also alternatively, a magnetically susceptible material can be electroplated onto a surface of a main body of the interventional medical device. Also alternatively, in embodiments in which an interventional medical device is formed of a metal, a portion of the main body of which it is desired to include a marker, can be hardened by cold working the material to increase magnetic susceptibility and create the marker. For example, a marker can be included on a tubular main body formed of a metal (e.g., annealed 304 Stainless Steel) by positioning a hardened wire within the inside diameter of the tubular member and against an internal surface of the tubular member, positioning a roller on an external surface of the tubular member such that it is aligned with the hardened wire, and rolling the roller along the length of the tubular member and along the hardened wire, using the hardened wire as a backing, to harden a portion of the tubular member and create a marker. Work hardening using a roller can also advantageously be performed on markers printed onto or adhered to a surface of the main body, such as an internal or external surface. Alternatively, in embodiments in which an interventional medical device is formed of a metal tubular main body, a portion of the main body of which it is desired to include a marker can include a filler material. For example, in methods of making an interventional medical device described below, a tubular main body is formed by rolling a ribbon of material longitudinally to form a c-shaped intermediate member having opposing portions and a longitudinal void disposed between the opposing portions. Subsequently, a laser is utilized to melt a filler material, such as a magnetically susceptible material, and fill the void between the edges of the opposing portions of the c-shaped main body.

While the marker 50 has been described as a material incorporated into the material forming the main body 14 and as extending along the entire axial length 19 of the main body 14, a marker can comprise any suitable material, in any form, having any suitable configuration, and can be attached to a main body in any suitable manner. Selection of a suitable material for a marker, a suitable configuration for a marker, and of a method or technique to attach a marker to a main body of an interventional medical device can be based on various considerations, including the type of material forming a main body and/or a marker. Examples of various materials considered suitable to form a markers, configurations considered suitable for a marker, and of methods and techniques for attaching a marker to a main body of an interventional medical device are described herein.

In this example, a marker extending the entire length of the main body, such as marker 50 in the embodiment illustrated in FIG. 1, can be obtained. Alternative lengths can be used, such as a length that is less than fifty percent of the axial length of the main body, a length that is about fifty percent of the axial length of the main body, a length that is more than fifty percent of the axial length of the main body, a length that is less than seventy-five percent of the axial length of the main body, a length that is about seventy-five percent of the axial length of the main body, and a length that is more than seventy-five percent of the axial length of the main body. A length that is more than fifty percent of the axial length of the main body is considered advantageous at least because of the advantageous imaging properties it provides. A length that is equal to the entire axial length of the main body is considered advantageous at least because of the desirable manufacturability it provides.

Any suitable number of markers can be included in an interventional medical device according to an embodiment. While the first example interventional medical device includes one marker 50, an interventional medical device according to a particular embodiment can include any number of markers considered suitable for the intended use of the particular interventional medical device and a skilled artisan will be able to identify a suitable number of markers based on various considerations, including the overall size and configuration of the interventional medical device, the intended use of the interventional medical device, and any desired goals or objectives for visualizing the medical device under MRI. Examples of suitable numbers of markers for inclusion in an interventional medical device according to an embodiment include one marker, two markers, a plurality of markers, three markers, four markers, five markers, six markers, seven markers, eight markers, nine markers, ten markers, more than ten markers, and any other number considered suitable for a particular embodiment. Furthermore, in embodiments that include two or more markers, the markers can be spaced from each other by a desired distance. For example, in an interventional medical device having three markers, the first marker can be spaced from the second marker by a first distance and the second marker can be spaced from the third marker by a second distance. The first and second distances can be the same or can be different.

Figure 2:
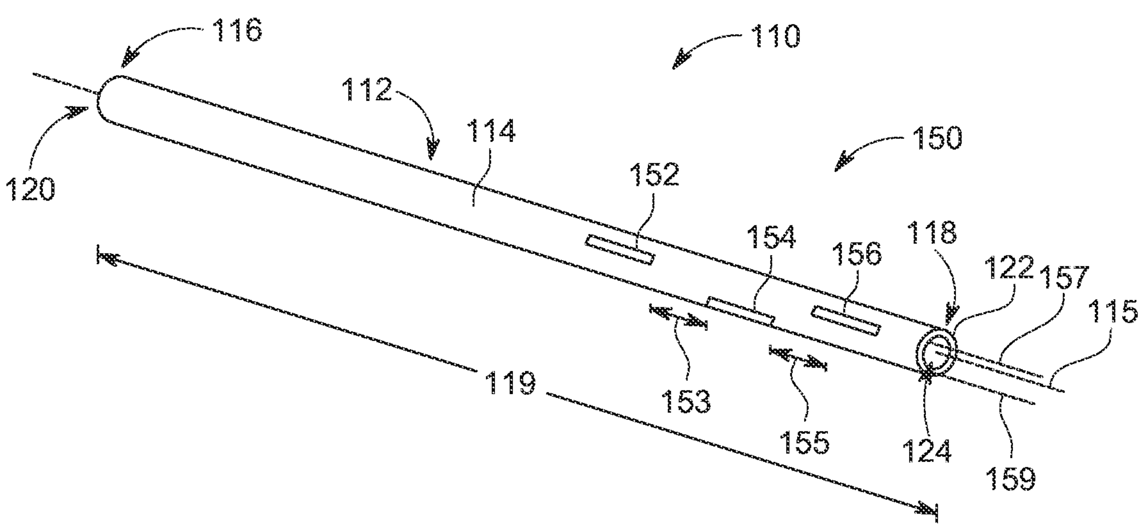
FIG. 2 is a perspective view of a second example interventional medical device.

FIG. 2 illustrates a second example interventional medical device 110. In this example, the interventional medical device 110 is an elongate tubular member 112.

The elongate tubular member 112 has a main body 114 that has a central lengthwise axis 115, a proximal end 116, a distal end 118, an axial length 119, and defines a proximal opening 120, a distal opening 122, and a lumen 124 that extends from the proximal opening 120 to the distal opening 122. A plurality of markers 150 is disposed along a portion of the axial length 119 of the main body 114 and parallel to the lengthwise axis 115. Each marker of the plurality of markers 150 is attached to the main body 114. In the illustrated embodiment, the elongate tubular member 112 is formed of a polymer and each marker 150 of the plurality of markers comprises a material incorporated into the material forming the main body 114.

In the illustrated embodiment, the plurality of markers 150 include a first marker 152, a second marker 154, and a third marker 156. The first marker 152 is spaced from the second marker 154 by a first distance 153 and the second marker 154 is spaced from the third marker 156 by a second distance 155. The first distance 153 is greater, and different, than the second distance 155. Each marker of the plurality of markers 150 is parallel to the lengthwise axis 115 of the main body 114. The first marker 152 and the third marker 156 are disposed along a first axis 157 that is disposed parallel to the lengthwise axis 115 and the second marker 152 is disposed along a second axis 159 that is disposed parallel to the lengthwise axis 115. The first and second axes 157, 159 are offset from one another on the main body 114 relative to the lengthwise axis 115.

The markers 152, 154, 156 of the plurality of markers 150 can be identical to each other with respect to physical properties, characteristics, and magnetic susceptibility. Alternatively, though, the markers 152, 154, 156 of the plurality of markers 150 can differ from each other, or from at least one other marker in the plurality of markers, in one or more of their physical properties, characteristics, and magnetic susceptibility. For example, each of the markers 152, 154, 156 of the plurality of markers 150 can have the same physical dimensions, including length, width, and thickness, and, as a result, the same volume. Alternatively, the markers 152, 154, 156 of the plurality of markers 150 can differ from each other, or from at least one other marker in the plurality of markers, in one or more of their physical properties, characteristics, and magnetic susceptibility. For example, discrete markers having different physical dimensions can be used in a plurality of markers in an embodiment. Also, discrete markers having different geometries can be used in a plurality of markers in an embodiment. Also, discrete markers having different magnetic susceptibilities can be used in a plurality of markers in an embodiment. For example, markers in a plurality of markers can be subjected to different degrees of work hardening to provide different magnetic susceptibilities to the markers. This is considered advantageous at least because it provides an ability to distinguish the markers of a plurality of markers in an interventional medical device when used under MRI.

Figure 3:
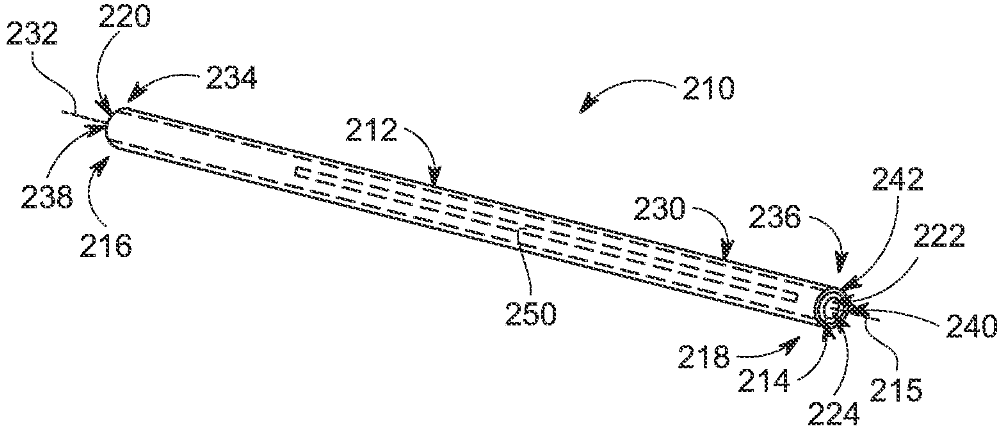
FIG. 3 is a perspective view of a third example interventional medical device.

FIG. 3 illustrates a third example interventional medical device 210. In this example, the interventional medical device 210 is an elongate tubular member 212.

The elongate tubular member 212 has a first main body 214 and a second main body 230. The first main body 214 has a central lengthwise axis 215, a proximal end 216, a distal end 218, and defines a proximal opening 220, a distal opening 222, and a lumen 224 that extends from the proximal opening 220 to the distal opening 222. The second main body 230 has a central lengthwise axis 232, a proximal end 234, a distal end 236, and defines a proximal opening 238, a distal opening 240, and a lumen 242 that extends from the proximal opening 238 to the distal opening 240. A marker 250 is disposed along a portion of the axial length of the first main body 214 and parallel to the central lengthwise axis 215 of the first main body 214. The marker 250 is attached to an external surface of the first main body 214. In the illustrated embodiment, the marker 250 is formed of Gadolinium. Also in this embodiment, the marker 250 comprises an elongate strip of material having an axial length that is greater than half the axial length of the first main body 214. The marker 250 has an axial length that is greater than three-fourths the axial length of the first main body 214. The second main body 230 is bonded over the external surface of the first main body 214 such that the marker 250 is shielded from contact with blood or a bodily passages during use.

Figure 4:
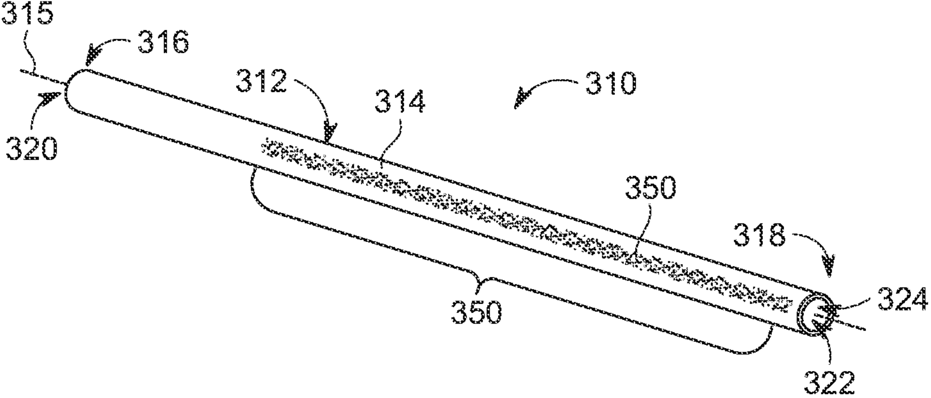
FIG. 4 is a perspective view of a fourth example interventional medical device.

FIG. 4 illustrates a fourth example interventional medical device 310. In this example, the interventional medical device 310 is an elongate tubular member 312.

The elongate tubular member 312 has a main body 314 that has a central lengthwise axis 315, a proximal end 316, a distal end 318, and defines a proximal opening 320, a distal opening 322, and a lumen 324 that extends from the proximal opening 320 to the distal opening 322. In the illustrated embodiment, the main body 314 is formed of 304 Stainless Steel. A marker 350 is disposed along a portion of the axial length of the main body 314 and parallel to the central lengthwise axis 315 of the main body 314. In the illustrated embodiment, the marker 350 comprises a portion of the main body 314 that includes dimpling or peening such that individual areas of the main body 314 have been work hardened and, as a whole, result in the marker 350. A localized section of the main body 314 can be work hardened by cold working the main body axially, such as by using a rotary swaging machine. In an alternative embodiment, an elongate tubular member can comprise first and second tubular members. The first tubular member formed of a first material (e.g., Inconel) is disposed within the second tubular member, which is formed of a second, different material (e.g., 304 Stainless Steel). The second tubular member can include dimpling or peening, as described herein, to provide discrete areas of increased hardness to increase the magnetic susceptibility.

The example interventional medical devices described herein are considered advantageous at least because they provide passive trackability of the device during treatment and under MRI. For example, in embodiments in which the interventional medical device has a marker disposed along its entire axial length, the entire device length is visible during use and under MRI. In procedures in which several devices are being used simultaneously during treatment, the interventional medical devices described herein allow for the interventional medical devices to be distinguished from the other devices. Furthermore, the inclusion of a marker along a portion, or the entirety, of the axial length of an interventional medical device, as described herein, provides conspicuity along the length of the device without interfering with the visualization of anatomical features during use. Moreover, since the markers described herein are passive, they eliminate any need to include long conductive structures necessary for functioning of active MR visualization devices, which are complex electronic components that must be connected to the accessory coil ports on the MR scanner.

A main body of an interventional medical device can be formed of any suitable material and selection of a suitable material to form a main body of an interventional medical device can be based on various considerations, including the intended use of the interventional medical device. Examples of MRI compatible materials considered suitable to form a main body of an interventional medical device include biocompatible materials, materials that can be made biocompatible, metals, electrically insulating materials, electrically non-conducting materials, non-magnetic materials, shape memory alloys, including nickel-titanium alloys such as Nitinol, stainless steel, including Austenitic stainless steel, stainless steel containing Iron, stainless steel including austenitic nickel-chromium-based alloys (e.g., Inconel, a registered trademark of Special Metals Corporation), 304 Stainless Steel, 316 stainless steel, cobalt chromium, cobalt chromium alloys, titanium, thermoplastics, polymers, PEEK, carbon-filled PEEK, ceramics, magnetized recording wire, polymers, the materials described herein, combinations of the described herein, and any other material considered suitable for a particular embodiment.

Any marker included in an interventional medical device, such as those described herein, has properties that produce visual artifacts during MRI procedures in which the interventional medical device is imaged. These visual artifacts can be used to determine placement of the interventional medical device relative to other portions of an MRI image, such as portions of a body vessel into which the interventional medical device has been advanced. An interventional medical device can include any suitable type and number of markers that allow for visualization of the main body in a magnetic resonance image and for device conspicuity without obscuring target tissue during treatment (e.g., biopsy, removal). A marker included in a main body of an interventional medical device can be attached to the main body using any suitable technique and be formed of any suitable material. Examples of techniques considered suitable to attach a marker to a main body of an interventional medical device include pressing, welding, using adhesives, including a marker material within the material forming a main body, and any other method or technique considered suitable for a particular embodiment. Examples of materials considered suitable to form a marker include biocompatible materials, materials that can be made biocompatible, MRI compatible materials, magnetically susceptible materials, including paramagnetic and ferromagnetic materials, metals, electrically insulating materials, electrically non-conducting materials, shape memory alloys, including nickel-titanium alloys such as Nitinol, Nickel Iron alloys such as Mu-Metal, stainless steel, including Austenitic stainless steel, stainless steel containing Iron, stainless steel including Inconel, cobalt chromium, cobalt chromium alloys, Inconel, titanium, ferromagnetic passive materials, ferromagnetic or paramagnetic compounds, such as those in powder form, Tantalum powder, Barium Sulfate, Bismuth Oxychloride, Tungsten, Iron Oxide nanoparticles, functionalized magnetite, Gadolinium, ink, ink containing magnetic particles, ink containing Iron Oxide nanoparticles, ink containing Iron Oxide nanoparticles bound to phospholipids, the materials described herein, combinations of the described herein, and any other material considered suitable for a particular embodiment. Furthermore, a marker can comprise any suitable structure attached to a main body of an interventional medical device or any suitable treatment imparted on a main body of an interventional medical device. For example, a marker can include bands of material, magnetic inks, sputtered magnetite marks of varying shapes and/or configurations, swaging, dimpling and/or peening the material that forms a main body of an interventional medical device (e.g., annealed 304 stainless steel), or a combination of these. Additional examples of markers considered suitable to include in an interventional medical device are described in U.S. patent application Ser. No. 16/454,905, filed on Jun. 27, 2019, which is hereby incorporated by reference in its entirety for the purpose of describing markers considered suitable to include in an interventional medical device. Any marker included in an interventional medical device can be identified by a unique pattern recognized and transformed into a virtual instrument within a program and displayed on a screen.

Various imaging methods, methods of performing interventional medical treatment under MRI, and methods of making interventional medical devices are described herein. While the methods described herein are shown and described as a series of acts, it is to be understood and appreciated that the methods are not limited by the order of acts, as some acts may in accordance with these methods may be omitted, occur in the order shown or described, occur in different orders, or occur concurrently with other acts described herein.

Figure 5:
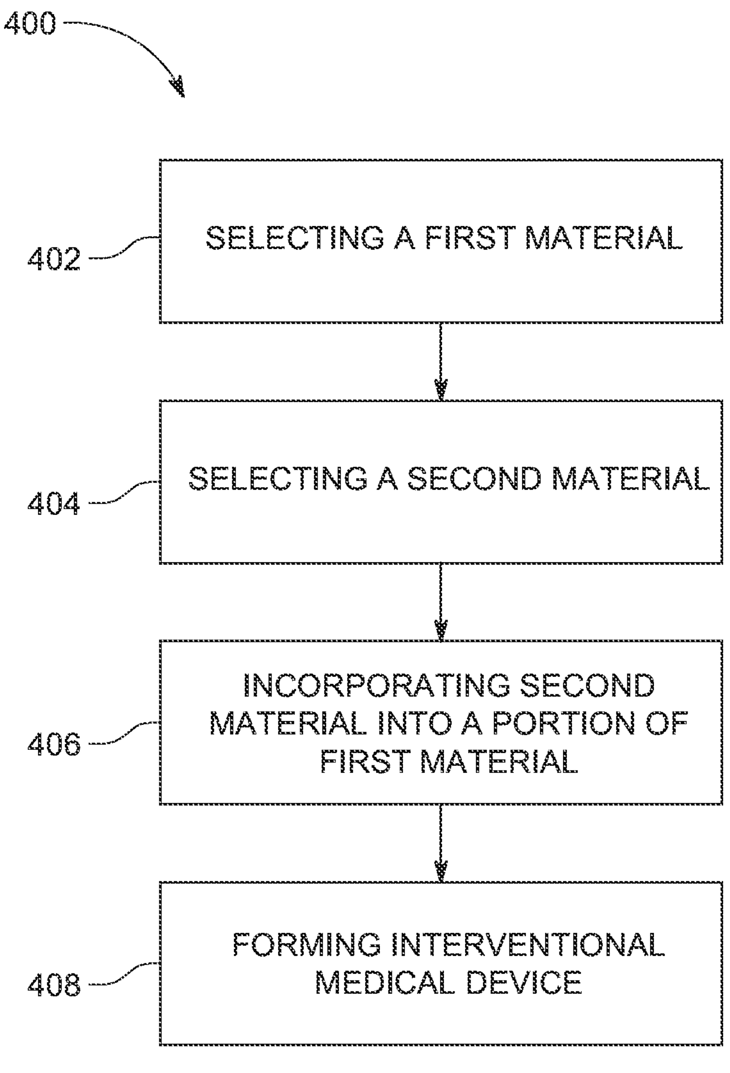
FIG. 5 is a schematic illustration of an example method of making a medical device.

FIG. 5 is a schematic illustration of an example method 400 of making a medical device.

An initial step 402 comprises selecting a first material to form an interventional medical device. Another step 404 comprises selecting a second material to form a marker to be included in a portion of the interventional medical device. Another step 406 comprises incorporating the second material into a portion of the first material. Another step 408 comprises forming the first and second materials into a desired structure to form the interventional medical device.

Step 402 of selecting a first material can be accomplished by identifying a material for which it is desirable to form an interventional medical device that includes a marker for purposes of using the interventional medical device with MRI. The first material can comprise any material considered suitable to form an interventional medical device or an elongate member of an interventional medical device, such as those described herein.

Step 404 of selecting a second material can be accomplished by identifying a material for which it is desirable to form a marker to be included in an interventional medical device for purposes of using the interventional medical device with MRI. The second material can comprise any magnetically susceptible material considered suitable to form a marker, such as those described herein.

Step 406 of incorporating the second material into a portion of the first material can be accomplished using any suitable method or technique of incorporating a second material into a first material such that the second material provides a desired marker for the interventional medical device as described herein. Selection of a suitable method or technique can be based on various considerations, such as the properties of the first material, the second material, or both. For example, step 406 can be accomplished by dispersing a second material, such as a powdered ferromagnetic compound, a powdered paramagnetic compound, Iron oxide nanoparticles, or functionalized magnetite, into a first material, such as a polymer. This approach changes the way in which the compound behaves in a magnetic field and influences the spin of the Hydrogen protons within the vicinity of the compound allowing for conspicuity under MRI. Step 406 is advantageously performed prior to initiation of step 408. Incorporating the second material into a portion of the first material, by performing step 406, prior to the final step of the method 400 of making an interventional medical device is considered advantageous at least because it incorporates the material of the marker or markers, the second material, into the first material prior to the final step of the fabrication process for the medical device.

A second material can be incorporated into any suitable portion of a first material and selection of a suitable portion of a first material to incorporate a second material can be based on various considerations, including the intended use of the interventional medical device being formed. Examples of portions of a first material considered suitable to incorporate a second material include along an entire axial length but only a portion of a width, along a portion of an axial length and a portion of a width, along a plurality of portions of an axial length, the portions described herein, and any other portion considered suitable for a particular embodiment.

As an alternative to step 406 of incorporating the second material into a portion of the first material, the second material can be disposed on the first material, which can include attaching the second material to the first material. For these methods, any suitable method or technique for disposing a material onto another material, and advantageously attaching the first material to the second material, can be used, including adhering, printing, electroplating, and other suitable methods or techniques.

Step 406, and optionally step 404 if additional selecting is required, can be repeated any desirable number of times if it is desired to include multiple markers, such as a plurality of markers, in an interventional medical device. In these examples, an individual instance of each of step 404 and/or 406 can be performed to provide multiple markers that have the same or different physical properties, characteristics, and magnetic susceptibility, as described above. Also in these examples, additional steps can be included to produce a desired difference in one or more the physical properties, characteristics, and magnetic susceptibility of the markers. For example, individual markers can be can be subjected to different types and/or degrees of work hardening to provide different magnetic susceptibilities to the markers. This is considered advantageous at least because it provides an ability to distinguish the markers of a plurality of markers in an interventional medical device when used under MRI.

Step 408 of forming the first and second materials into a desired structure to form the interventional medical device can be accomplished using any suitable method or technique of forming the first and second materials into a desired structure. Selection of a suitable method or technique can be based on various considerations, such as the properties of the first and second materials. Examples of methods and techniques considered suitable to form an interventional medical device include casting, injection molding, extruding, and any other method or technique considered suitable for a particular embodiment.

The methods described herein are useful in the making of a variety of interventional medical devices and precursors to such interventional medical devices, including guidewires, catheters, needles, sheaths, snares, and other interventional medical devices.

Figure 6:
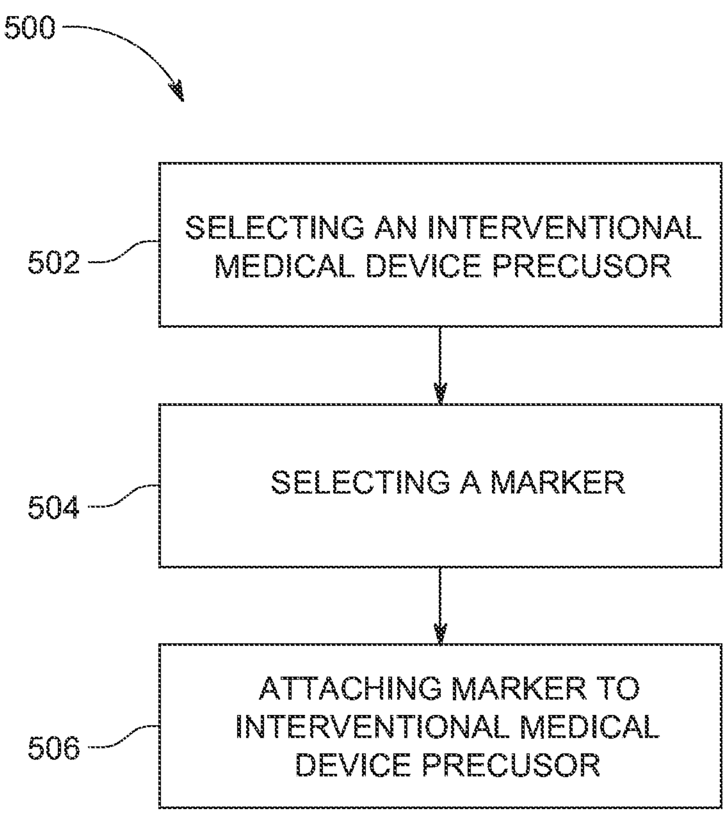
FIG. 6 is a schematic illustration of another example method of making a medical device.

FIG. 6 is a schematic illustration of another example method 500 of making a medical device.

An initial step 502 comprises selecting an interventional medical device precursor that has a main body that has proximal and distal ends. Another step 504 comprises selecting a marker. Another step 506 comprises attaching the marker to the main body.

Step 502 of selecting an interventional medical device precursor can be accomplished by identifying an interventional medical device for which it is desirable to attach a marker for purposes of using the interventional medical device with MRI. The interventional medical device can be any suitable interventional medical device, or a precursor to such an interventional medical device. Examples of suitable interventional medical devices include guidewires, catheters, needles, sheaths, snares, and other suitable interventional medical devices. Also, implantable medical devices, such as stents, frames, valves, filters, occluders, and other devices can be selected in this step.

Step 504 of selecting a marker can be accomplished by identifying a material for which it is desirable to form a marker to be included in an interventional medical device for purposes of using the interventional medical device with MRI. The marker can comprise any material and/or structure considered suitable to form a marker, such as those described herein. Alternatively, step 504 can be accomplished by selecting a method or technique of imparting marker properties into a material that forms an interventional medical device precursor.

Figure 7:
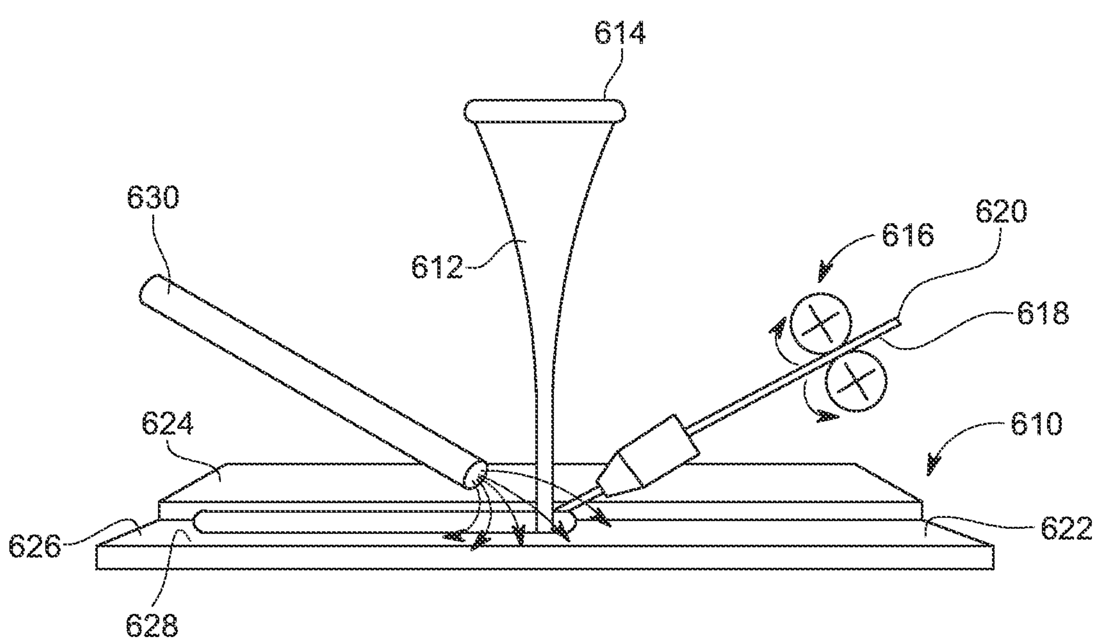
FIG. 7 is a partial perspective view of an example system useful in incorporating a marker into a main body of an interventional medical device.

Step 506 of attaching the marker to the main body can be accomplished using any suitable method or technique of attaching a marker to a main body. Selection of a suitable method or technique can be based on various considerations, such as the properties of the interventional medical device precursor and/or the marker. For example, step 506 can be accomplished as described herein, by printing the marker (e.g., magnetic ink, magnetic ink containing magnetic particles) onto a surface of the main body, such as an external or internal surface, applying the marker (e.g., formed of Gadolinium) to a surface of the main body, such as an external or internal surface, and/or welding the marker to the main body. In embodiments in which Gadolinium, or other material, is used to form a marker, an optional step comprises attaching a second main body to the first main body such that the marker is completely covered and shielded from contact with a bodily passage and/or blood during use. In some embodiments, additional steps can be included. For example, a step of rolling a ribbon of material, such as Inconel, along a lengthwise axis of the ribbon to form a c-shaped intermediate body can be included. In these methods, a step of melting the material forming the marker (e.g., Inconel, 304 Stainless Steel) using a laser can be included. In these methods, after the step of rolling a ribbon of material and after the step of melting the material forming the marker, a step of disposing the melted material into the void to fill the void between the edges of the c-shaped tubular main body using the melted material is advantageously included. The steps of melting and filling can be performed sequentially but are advantageously performed simultaneously. FIG. 7 illustrates an example system 610 considered suitable for incorporating a marker into a main body using this method. The system 610 includes a laser beam 612 focused by a focused optic 614, a wire feed apparatus 616 that feeds a wire 618 of the second material 620 to a void 622 between opposing sides 624, 626 of the first material 628, which has been rolled from a ribbon to a c-shaped body having the void 622 between opposing sides 624, 626. A gas nozzle 630 delivers a shielding gas to the point of interaction between the laser beam 612 and the wire 618.

Figure 8:
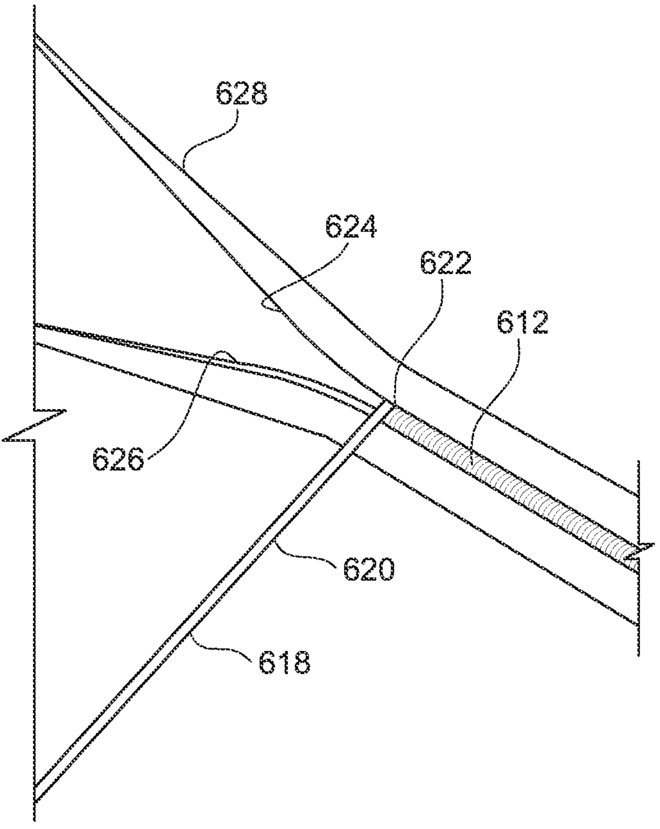
FIG. 8 is a partial perspective view of an example marker being attached to an example main body of an interventional medical device.

FIG. 8 illustrates the wire 618 of the second material 620 being melted into longitudinal void 622 between opposing sides 624, 626 of the first material 628, which is being rolled from a ribbon configuration to a c-shaped body having the void 622 between opposing sides 624, 626. In this example, and in other example methods in which a second material is welded or otherwise attached to the first material, the welding or attaching can use another material that includes the second material 620, or that incorporates the second material, a magnetically susceptible material, during attachment to the first material.

Figure 9:
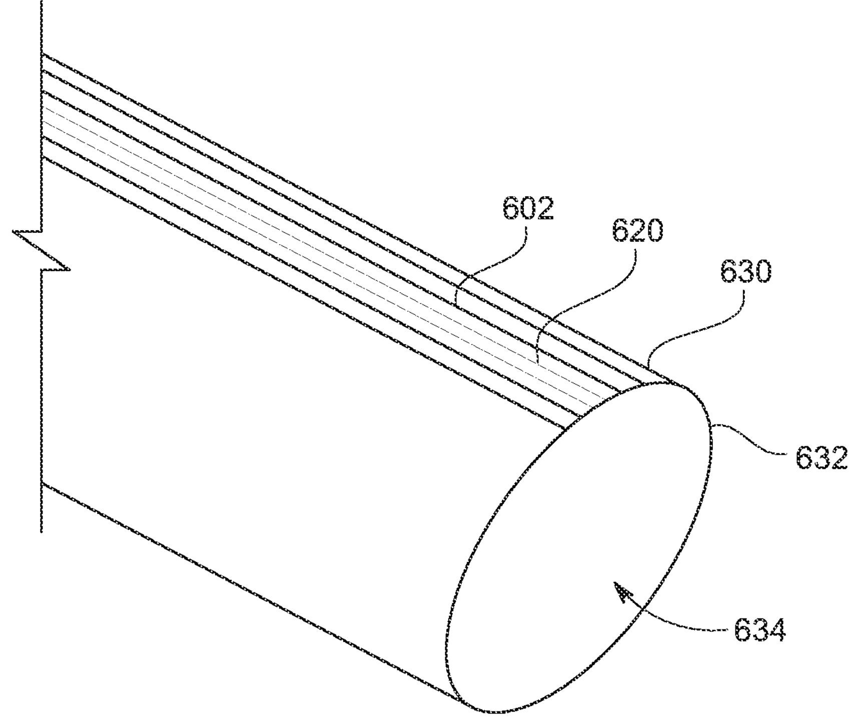
FIG. 9 is a partial perspective view of another example interventional medical device.

In embodiments in which a marker is welded to a tubular main body, additional steps can include rolling a ribbon of the first material longitudinally to form a c-shaped intermediate member having opposing portions and a longitudinal void disposed between the opposing portions, melting the material forming the marker (e.g., a magnetically susceptible materials such as 304 Stainless Steel) such as by using a laser; filling the void between the opposing portions of the c-shaped intermediate member to form a tubular main body; and cold working a portion, or the entirety, of the marker material to increase magnetic susceptibility of the marker in the interventional medical device. The step of cold working a portion, or the entirety, of the marker material can be accomplished, for example, by placing a hardened wire within a lumen defined by the tubular main body and rolling the marker material against the hardened wire. As one example, FIG. 9 illustrates a marker 602 in which the second material 620 comprises stainless steel that has been disposed in a longitudinal void in a c-shaped intermediate member 630 to form tubular main body 632. The stainless steel has been work hardened along the length of the marker, such as by rolling or a plug drawn through the lumen 634 of the main body 632, as described above.

In embodiments in which a method or technique is used to impart marker properties into a material that forms an interventional medical device precursor, step 506 can include a suitable work hardening method or technique to harden areas along the length of the interventional medical device of which it is desired to include a marker to increase magnetic susceptibility. Examples of suitable work hardening methods or techniques include swaging, rotary swaging, and dimpling or peening.

All methods can include appropriate finishing steps. For example, for methods that result in formation of tubular members, a plug can be passed through the internal lumen of the tubular member to flatten the region of the tubular member that includes the weld. Inclusion of a step of passing a plug through the internal lumen of the tubular member is considered advantageous at least because it removes any inwardly directed material that may have resulted from the weld or attachment process. Furthermore, the step of passing a plug through the internal lumen of the tubular member is considered advantageous because it flattens the portion of the tubular member containing the weld or attachment, which can contribute to the work hardening of this portion of the tubular member. In some example methods in which a ribbon of a first material is rolled into a c-shaped elongate member, a side of the ribbon that becomes disposed in the internal of the resulting c-shaped member can be electroplated, such as with Nickel, before a welding step or attaching step is performed.

Figure 10:
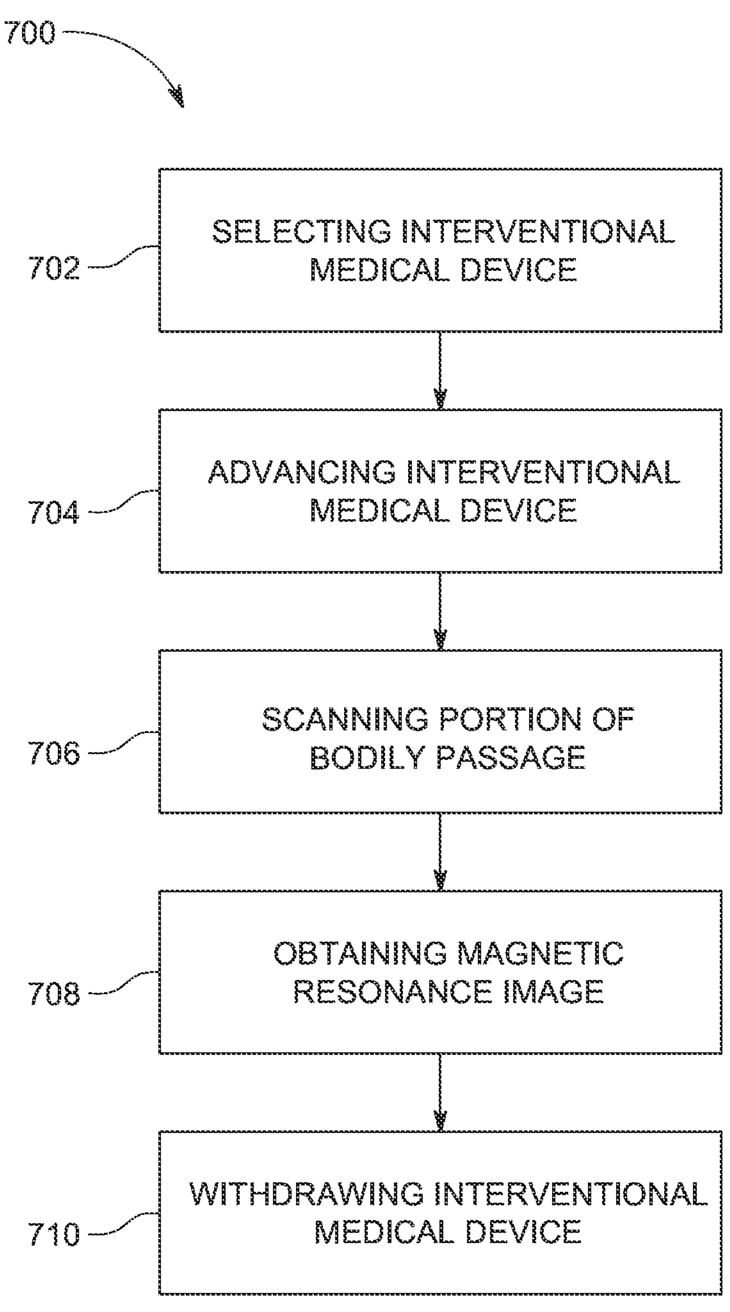
FIG. 10 is a schematic illustration of an example imaging method.

FIG. 10 is a schematic illustration of an example imaging method 700.

An initial step 702 comprises selecting an interventional medical device having a main body that has proximal and distal ends and a marker attached to the main body. Another step 704 comprises advancing the distal end of the interventional medical device to a first location within a bodily passage of a patient and until the marker is disposed at a second location within the bodily passage. Another step 706 comprises scanning a portion of the bodily passage that includes the first and second locations within the bodily passage using a magnetic resonance scanner. Another step 708 comprises obtaining a magnetic resonance image of the portion of the bodily passage such that the image includes an artifact indicative of the presence of the marker within the portion of the bodily passage. For this step 708, a single still image can be obtained. Also, and optionally, this step 708 can be repeated any desired number of times to obtain multiple magnetic resonance images that can be grouped as a cine to show motion and/or step 708 can comprise obtaining a live image, such as being completed under live real-time MRI visualization. Another step 710 comprises withdrawing the interventional medical device from the bodily passage.

Step 702 of selecting an interventional medical device can be accomplished by selecting any suitable interventional medical device, such as those described herein, or those formed using the methods described herein. A bodily passage can include any suitable portion of a body, including existing bodily passages, bodily lumens, and/or bodily passages created through tissues layers and/or fascia using a device described herein.

Figure 11:
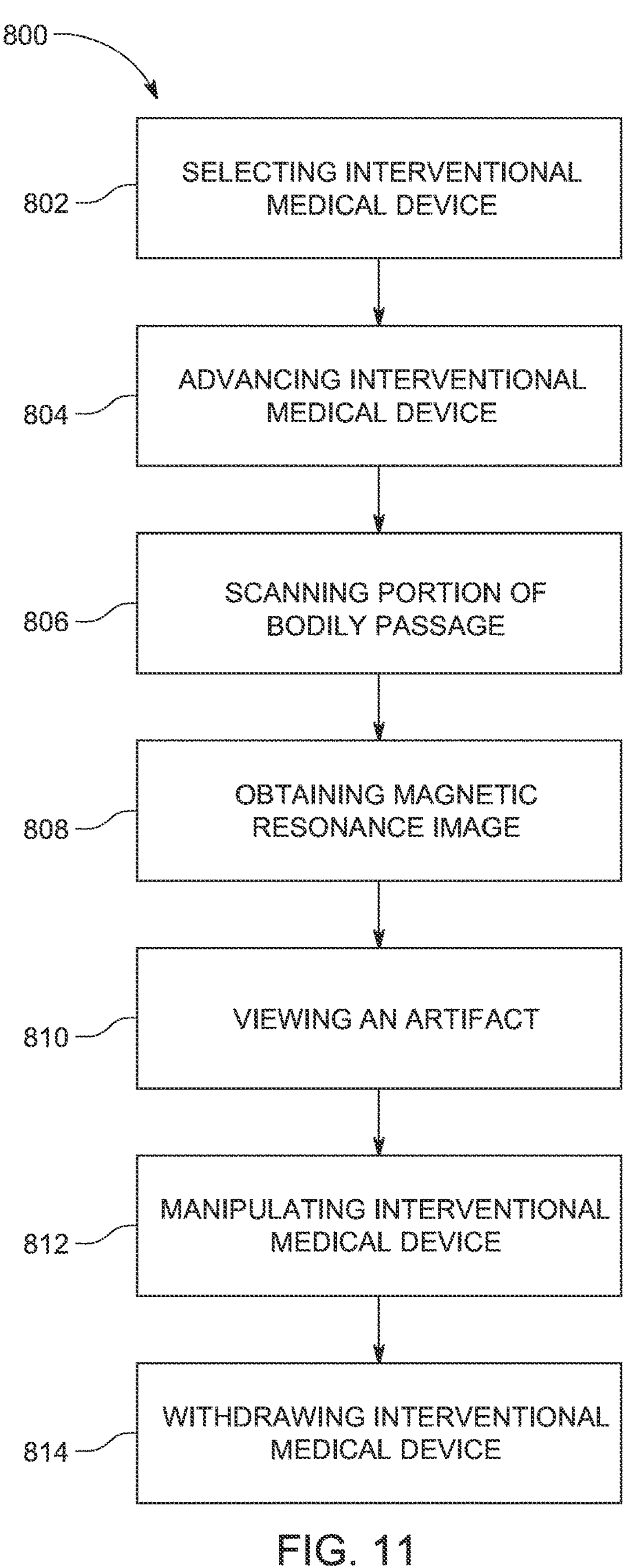
FIG. 11 is a schematic illustration of an example method of performing an interventional medical treatment.

FIG. 11 is a schematic illustration of an example method 800 of performing an interventional medical treatment.

An initial step 802 comprises selecting an interventional medical device having a main body that has proximal and distal ends and a marker attached to the main body. Another step 804 comprises advancing the distal end of the interventional medical device to a first location within a bodily passage of a patient and until the marker is disposed at a second location within the bodily passage. Another step 806 comprises scanning a portion of the bodily passage that includes the second location within the bodily passage using a magnetic resonance scanner. Another step 808 comprises obtaining a magnetic resonance image of the portion of the bodily passage such that the image includes an artifact indicative of the presence of the marker within the portion of the bodily passage. Another step 810 comprises viewing an artifact in the image generated by the presence of the marker. Another step 812 comprises manipulating the interventional medical device based on the location of the artifact relative to the bodily passage. Another step 814 comprises withdrawing the interventional medical device from the bodily passage.

Step 812 is performed in a manner that achieves, or that contributes to the achievement of, a desired clinical outcome of the method 800 of performing an interventional medical treatment. As such, the nature of the step 812 of manipulating the interventional medical device will depend on the nature of the interventional medical device and the desired clinical outcome. Examples of suitable actions that can be performed for this step include, but are not limited to, axially advancing the interventional medical device within the bodily passage, rotating the interventional medical device within the bodily passage, radially expanding the interventional medical device within the bodily passage, and axially withdrawing a portion of the interventional medical device to allow another portion of the interventional medical device, or a second medical device associated with the interventional medical device, to radially expand within the bodily passage. In alternative embodiments, step 812 can be omitted from method 800 when manipulation of the interventional medical device is not desired.

Any of the steps being performed by a magnetic resonance scanning can be accomplished using any suitable magnetic resonance scanner, such as conventional magnetic resonance scanners, magnetic resonance scanners that utilize 0.55 T fields, 1.5 T fields, 3 T fields, fields between about 0.055 T and 1.5 T, fields less than 1 T, and any other magnetic resonance scanner considered suitable for a particular embodiment.

Any of the steps being performed within a bodily passage can be accomplished utilizing any suitable portion of a patient and selection of a suitable portion of a patient to scan can be based on various considerations, including the treatment intended to be performed. Examples of portions of a patient considered suitable include bodily passages disposed within the extremities (e.g., arms, legs), chest, breast, spine, neck, head, abdomen, pelvis, prostate, peri-prostatic structures, tissue surrounding the portions described herein, and/or any other portion of the patient considered suitable for a particular embodiment.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular arrangement of elements and steps disclosed herein have been selected by the inventor(s) simply to describe and illustrate examples of the invention and are not intended to limit the scope of the invention or its protection, which is to be given the full breadth of the appended claims and any and all equivalents thereof.

What is claimed is:

1. A method of making a medical device useful in procedures performed under magnetic resonance imaging, said method comprising:
- selecting a first material to form an interventional medical device for use under magnetic resonance imaging;
- selecting a second material to form a marker to be included in a portion of the interventional medical device, the second material comprising a magnetically susceptible material that is different from the first material;
- incorporating the second material into a portion of the first material such that a combination of the first material and the second material is visible under magnetic resonance imaging and distinguishable from the first material under magnetic resonance imaging;
- after incorporating the second material into a portion of the first material, forming the first and second materials into a tubular member having an internal lumen to form the interventional medical device for use under magnetic resonance imaging; and
- attaching a second marker to the interventional medical device.

2. The method of claim 1, wherein the first material comprises a ribbon having a lengthwise axis;
- further comprising rolling the ribbon along the lengthwise axis to form a c-shaped intermediate member having opposing portions and a longitudinal void disposed between the opposing portions; and
- wherein the step of incorporating the second material into a portion of the first material comprises disposing the second material into the longitudinal void.

3. The method of claim 2, wherein the second material comprises a wire.

4. The method of claim 1, further comprising disposing the tubular member into a second tubular member.

5. The method of claim 1, wherein the first material comprises a magnetic resonance imaging compatible material.

6. The method of claim 5, wherein the first material comprises one of a nickel chromium alloy and a nickel titanium alloy.

7. The method of claim 6, wherein the second material comprises a paramagnetic material or a ferromagnetic material.

8. The method of claim 1, wherein the second material comprises a paramagnetic material or a ferromagnetic material.

9. The method of claim 8, wherein the second material comprises a powder.

10. The method of claim 1, further comprising cold working the second material to increase magnetic susceptibility.

11. The method of claim 10, wherein the step of cold working the second material is performed before the step of forming the first and second materials into a tubular member is performed.

12. The method of claim 10, wherein the step of cold working the second material is performed after the step of forming the first and second materials into a tubular member is performed.

13. The method of claim 10, wherein the step of cold working the second material is performed while the step of forming the first and second materials into a tubular member is performed.

14. The method of claim 1, wherein the step of incorporating the second material into a portion of the first material is repeated to form a second marker that is discrete from the marker; and
- further comprising work hardening the marker to increase the magnetic susceptibility of the marker by a first amount; and
- work hardening the second marker to increase the magnetic susceptibility of the second marker by a second amount that is different from the first amount.

15. The method of claim 1, wherein the second material comprises Barium Sulfate, Bismuth Oxychloride, Tungsten, Iron Oxide nanoparticles, functionalized magnetite, Gadolinium, Stainless Steel, Ferritic Stainless Steel, or 316 Stainless Steel.

16. The method of claim 1, wherein the second marker and the combination of the first material and the second material comprise discrete markers having different dimensions.

17. The method of claim 1, wherein the second marker and the combination of the first material and the second material comprise discrete markers having different geometries.

18. The method of claim 1, wherein the second marker and the combination of the first material and the second material have different magnetic susceptibilities.

19. The method of claim 1, wherein the interventional medical device has an axial length; and wherein the combination of the first material and the second material provides conspicuity along a portion of the axial length.

20. The method of claim 1, wherein the interventional medical device has an axial length; and wherein the combination of the first material and the second material provides conspicuity along the entirety of the axial length.

21. A method of making a medical device useful in procedures performed under magnetic resonance imaging, said method comprising:

selecting a first material to form an interventional medical device;

selecting a second material to form a marker to be included in a portion of the interventional medical device, the second material comprising a magnetically susceptible material that is different from the first material;

incorporating the second material into a portion of the first material;

forming the first and second materials into a desired structure to form the interventional medical device;

wherein the first material comprises a ribbon having a lengthwise axis;

further comprising rolling the ribbon along the lengthwise axis to form a c-shaped intermediate member having opposing portions and a longitudinal void disposed between the opposing portions;

wherein the step of incorporating the second material into a portion of the first material comprises disposing the second material into the longitudinal void;

wherein the second material comprises a wire;

further comprising a step of melting the wire.

22. A method of making a medical device useful in procedures performed under magnetic resonance imaging, said method comprising:

selecting a first material to form an interventional medical device;

selecting a second material to form a marker to be included in a portion of the interventional medical device, the second material comprising a magnetically susceptible material that is different from the first material;

incorporating the second material into a portion of the first material; and forming the first and second materials into a desired structure to form the interventional medical device;

wherein the first material comprises a ribbon having a lengthwise axis;

further comprising rolling the ribbon along the lengthwise axis to form a c-shaped intermediate member having opposing portions and a longitudinal void disposed between the opposing portions;

wherein the step of incorporating the second material into a portion of the first material comprises disposing the second material into the longitudinal void;

wherein the second material comprises a wire;

further comprising a step of melting the wire;

wherein the steps of melting the wire and incorporating the second material into a portion of the first material are performed sequentially.

23. A method of making a medical device useful in procedures performed under magnetic resonance imaging, said method comprising:

selecting a first material to form an interventional medical device;

selecting a second material to form a marker to be included in a portion of the interventional medical device, the second material comprising a magnetically susceptible material that is different from the first material;

incorporating the second material into a portion of the first material; and forming the first and second materials into a desired structure to form the interventional medical device;

wherein the first material comprises a ribbon having a lengthwise axis;

further comprising rolling the ribbon along the lengthwise axis to form a c-shaped intermediate member having opposing portions and a longitudinal void disposed between the opposing portions;

wherein the step of incorporating the second material into a portion of the first material comprises disposing the second material into the longitudinal void;

wherein the second material comprises a wire;

further comprising a step of melting the wire;

wherein the steps of melting the wire and incorporating the second material into a portion of the first material are performed simultaneously.

* * * * *